(12) United States Patent
Sugiura et al.

(10) Patent No.: US 10,774,186 B2
(45) Date of Patent: Sep. 15, 2020

(54) PHOTODEGRADABLE HYDROGEL, CULTURE DEVICE, METHOD FOR FORMING TISSUE, AND METHOD FOR SEPARATING CELLS

(71) Applicant: NATIONAL INSTITUTE OF ADVANCED INDUSTRIAL SCIENCE AND TECHNOLOGY, Tokyo (JP)

(72) Inventors: Shinji Sugiura, Tsukuba (JP); Masato Tamura, Osaka (JP); Toshiyuki Takagi, Tsukuba (JP); Kimio Sumaru, Tsukuba (JP); Toshiyuki Kanamori, Tsukuba (JP); Fumiki Yanagawa, Kawasaki (JP)

(73) Assignee: NATIONAL INSTITUTE OF ADVANCED INDUSTRIAL SCIENCE AND TECHNOLOGY (JP)

( * ) Notice: Subject to any disclaimer, the term of this patent is extended or adjusted under 35 U.S.C. 154(b) by 360 days.

(21) Appl. No.: 15/561,568

(22) PCT Filed: Apr. 4, 2016

(86) PCT No.: PCT/JP2016/061017
§ 371 (c)(1),
(2) Date: Sep. 26, 2017

(87) PCT Pub. No.: WO2016/159380
PCT Pub. Date: Oct. 6, 2016

(65) Prior Publication Data
US 2018/0086883 A1 Mar. 29, 2018

(30) Foreign Application Priority Data
Apr. 3, 2015 (JP) ................................. 2015-077159

(51) Int. Cl.
*C08J 3/075* (2006.01)
*C08G 81/00* (2006.01)
(Continued)

(52) U.S. Cl.
CPC .............. *C08J 3/075* (2013.01); *C08G 81/00* (2013.01); *C08J 3/246* (2013.01); *C12N 5/0012* (2013.01);
(Continued)

(58) Field of Classification Search
CPC ........ C08J 3/075; C08J 3/246; C08J 2371/02; C08J 2389/00; C08G 81/00;
(Continued)

(56) References Cited

U.S. PATENT DOCUMENTS

2014/0256831 A1    9/2014   Ito et al. ....................... 514/777
2016/0177030 A1    6/2016   Sugiura et al.

FOREIGN PATENT DOCUMENTS

JP    2012-080844 A    4/2012
JP    2014-226088 A    12/2014
(Continued)

OTHER PUBLICATIONS

International Search Report dated Jun. 21, 2016 in corresponding PCT International Application No. PCT/JP2016/061017.
(Continued)

*Primary Examiner* — Shane Fang
(74) *Attorney, Agent, or Firm* — Ostrolenk Faber LLP

(57) ABSTRACT

Provided are a photodegradable hydrogel in which cells can be embedded in the photodegradable gel without causing cytotoxicity when the cells are embedded in the photodegradable gel by allowing the cells to coexist at the time of preparation of the photodegradable gel, and which contains a protein as one of the main components; a culture device using the same; a method for forming tissue; and a method for separating cells. A photodegradable hydrogel is obtained by condensation of an alkyne group contained in a cyclooctyne ring or an azacyclooctyne ring of the following compound A with an azido group of the following compound B.
(Continued)

(Compound A) A compound is a photocleavable crosslinker which contains a main chain having a linear type- or a branched type- (of three or more branches) polyethylene glycol structure, a photodegradable nitrobenzyl group disposed at both terminals or a branched terminal of the main chain, and a group having a cyclooctyne ring or an azacyclooctyne ring disposed at a terminal side of the nitrobenzyl group. (Compound B) A compound is an azide-modified protein in which a main chain is a protein and at least some of an amino group present at lysine and arginine side chains of the main chain and an amino group present at a terminal of the main chain are modified with the azido group.

13 Claims, 14 Drawing Sheets

(51) Int. Cl.
    *C12N 11/04* (2006.01)
    *C08J 3/24* (2006.01)
    *C12N 5/00* (2006.01)
(52) U.S. Cl.
    CPC ......... *C12N 5/0018* (2013.01); *C12N 5/0068* (2013.01); *C12N 11/04* (2013.01); *C08J 2371/02* (2013.01); *C08J 2389/00* (2013.01); *C12N 2501/10* (2013.01); *C12N 2533/10* (2013.01); *C12N 2533/50* (2013.01); *C12N 2533/54* (2013.01); *C12N 2537/10* (2013.01); *C12N 2539/00* (2013.01)
(58) Field of Classification Search
    CPC .. C12N 5/0012; C12N 5/0018; C12N 5/0068; C12N 11/04; C12N 2501/10; C12N 2533/10; C12N 2533/50; C12N 2533/54; C12N 2537/10; C12N 2539/00
    See application file for complete search history.

(56) References Cited

FOREIGN PATENT DOCUMENTS

| WO | WO 2012/165462 A1 | 12/2012 |
|---|---|---|
| WO | WO 2014/188911 A1 | 11/2014 |
| WO | WO 2014/189370 A1 | 11/2014 |

OTHER PUBLICATIONS

Written Opinion dated Jun. 21, 2016 in corresponding PCT International Application No. PCT/JP2016/061017.
C.B. Hutson et al., "Synthesis and Characterization of Tunable Poly(Ethylene Glycol): Gelatin Methacrylate Composite Hydrogels," Tissue Engineering: Part A, 17, 1713-1723 (2011).
L. Schukur et al., "Directed Differentiation of Size-Controlled Embryoid Bodies Towards Endothelial and Cardiac Lineages in RGD-Modified Poly(Ethylene Glycol) Hydrogels," Adv. Healthcare Mat., 2, 195-205 (2013).
M. Tamura et al., "Optical cell separation from three-dimensional environment in photodegradable hydrogels for pure culture techniques," Sci. Rep. 4, 4793 (2014).
M.W. Tibbitt et al., "Controlled two-photon photodegradation of PEG hydrogels to study and manipulate subcellular interactions on soft materials," Soft Matter 6, 5100-5108 (2010).
A.M. Kloxin et al., "Photodegradable Hydrogels for Dynamic Tuning of Physical and Chemical Properties," Science, vol. 324, pp. 59-63 (2009).
F. Yanagawa et al., "Activated-Ester-Type Photocleavable Crosslinker for Preparation of Photodegradable Hydrogels Using a Two-Component Mixing Reaction," Adv. Healthcare Mat., in press, DOI:10.1002/adhm.201400180 (2014).
C.A. DeForest et al., "Cytocompatible click-based hydrogels with dynamically tunable properties through orthogonal photoconjugation and photocleavage reactions," Nature Chem. 3, 925-931 (2011).
M.A. Azagarsamy et al., "Bioorthogonal Click Chemistry: An Indispensable Tool to Create Multifaceted Cell Culture Scaffolds," ACS Macro Letters 2, 5-9, doi:10.1021/mz300585q (2013).
M.C. Miedel et al., "The use of fluorescamine as a detection reagent in protein microcharacterization," J. Biochem. Biophys. Methods 18, 37-52 (1989).
G. Ninan et al., "Physical, Mechanical, and Barrier Properties of Carp and Mammalian Skin Gelatin Films," J. Food Sci. 75, E620-E626, (2010).
K. Kikuchi et al., "Stepwise Assembly of Micropatterned Co-cultures Using Photoresponsive Culture Surfaces and Its Application to Hepatic Tissue Arrays," Biotechnol. Bioeng. 103, 552-561 (2009).
M. Giulbudagian et al., "Fabrication of thermoresponsive nanogels by thermo-nanoprecipitation and in situ encapsulation of bioactives," Polymer Chemistry, vol. 5, pp. 6909-6913 (2014).
V.X. Truong et al., "Photodegradable Gelatin-Based Hydrogels Prepared by Bioorthogonal Click Chemistry for Cell Encapsulation and Release," Biomacromolecules, vol. 16, pp. 2246-2253 (2015).

Scale bar: 200 μm

Diameter: I = 20μm, II = 30 μm, III = 45 μm, IV = 68 μm, V = 101
Line width of frame border: 10 μm Scale bar: 200 μm Diameter: I = 20μm, II = 30 μm, III = 45 μm, IV = 68 μm, V = 101
Line width of frame border: 10 μm

PHOTODEGRADABLE HYDROGEL, CULTURE DEVICE, METHOD FOR FORMING TISSUE, AND METHOD FOR SEPARATING CELLS

CROSS-REFERENCE TO RELATED APPLICATIONS

The present application is a 35 U.S.C. §§ 371 national phase conversion of PCT/JP2016/061017, filed Apr. 4, 2016, which claims priority to Japanese Patent Application No. 2015-077159, filed Apr. 3, 2015, the contents of which are incorporated herein by reference. The PCT International Application was published in the Japanese language.

TECHNICAL FIELD

The present invention relates to the field of materials engineering and particularly relates to a photodegradable gel which can be used for manufacturing complex and fine three-dimensional tissue, a culture device using the same, a method for separating cells, a method for forming tissue, and tissue.

BACKGROUND ART

In developing new substances and developing new uses of substances, it is important to verify the effects of the substances on the human body depending on the use form thereof. Among these, in developing pharmaceuticals, food additives, and the like, it is essential to verify what kind of effects these substances have on the human body.

For such verification, animal experiments and experiments at a cell level using cultured cells are generally carried out, but in accordance with technological advances, higher-throughput cell-level assays using cultured cells have been required.

On the other hand, in monolayer culture, which is generally used in a cell assay, the environment around the cells is greatly different from the environment in the animal body, and therefore there is a problem in that most functions which are expressed in the body are lost in such cultured cells.

In next-generation cell assay technologies, a tissue mimicking a three-dimensional structure in vivo is artificially reconstructed and a more reliable assay using tissue having a higher level of function is employed, and therefore, it is expected that a higher level of a vivo-vitro correlation can be obtained.

As a cell culture method, there is a method using hydrogel. A hydrogel has excellent characteristics as a carrier of cells such as high-water content, ease of adjusting mechanical properties, excellent nutrient diffuseness, and the like. An embedment culture method in which cells are cultured in a state where the cells are three-dimensionally dispersed inside a hydrogel is known as a method for enhancing the function of cells by interaction between cells and the hydrogel.

In the embedment culture method, it is known that a molecular structure of a polymer constituting a hydrogel greatly influences the function of cells. Particularly, many examples are known in which cells exhibit a high level of function in a hydrogel having, as a main component, a biological polymer including an extracellular matrix such as collagen, gelatin, laminin, and Matrigel.

It is known that collagen exists in various tissues in a living body and is a main component of an extracellular matrix, and it is known that many hydrogels containing collagen as a main component have cell adhesiveness. Cells that are likely to lose the function in a normal culture dish can maintain the function thereof by applying a collagen gel embedment culture method or a collagen gel sandwich culture method. Gelatin is a polymer of which water solubility increases by modifying collagen with acid, alkali, heat, and the like, and maintains cell adhesiveness while being modified, and therefore is used as a substrate for cell culture as same as collagen. Gelatin is inexpensive compared to collagen, and therefore is frequently used for coating of a culture dish. Matrigel is a cell culture substrate sold by Corning Incorporated, and various growth factors such as transforming growth factor (TG), epithelial cell growth factor (EGF), insulin-like growth factor (IGF), and fibroblast cell growth factor (FGF) are contained in addition to an extracellular matrix such as laminin and collagen which are main components thereof.

On the other hand, it is known that cell growth and function do not increase in a hydrogel containing a synthetic polymer such as polyethylene glycol as a main component (NPL 1). It is known that in the hydrogel of a synthetic polymer, arginine-glycine-aspartic acid (RGD) peptide, which is one of the cell adhesion factors of collagen, is modified into a hydrogel in order to impart cell adhesiveness, and therefore cell function can be increased (NPL 2).

A hydrogel can be imparted with photodegradability by incorporating a photodegradable group into the molecule. A photodegradable gel which can be processed by light has been developed using such photodegradability. Examples of a photodegradable gel include a photodegradable gel which contains polyethylene glycol as a main chain and a nitrobenzyl group in the molecule. It is known that the physical properties of a hydrogel formed from a polymeric monomer having such a constitution can be temporally and spatially controlled by light irradiation, and that such photodegradation has no significant cytotoxicity with respect to living cells.

By culturing cells in such a photodegradable gel, cultured cells can be easily extracted from the gel by irradiating the gel with light to degrade the gel. By using the above, for example, only cells at a specific position can be extracted by irradiating only the specific position of the gel with light so that the gel degrades, and therefore, it is possible to separate a specific cell of the cultured cell group (NPL 3).

As a method for preparing a photodegradable gel, a method using radical polymerization is known (NPLs 4 and 5). In a case of using radical polymerization, when polymerization is carried out in the presence of oxygen, a reaction of gelation may be inhibited in some cases due to oxygen. Furthermore, a radical damages cells and physiologically active substances. Since a polymer compound which can be used as a main chain is limited to a polymeric monomer capable of undergoing radical polymerization, use thereof is limited.

The inventors of the present invention have developed a photocleavable crosslinker capable of forming a photodegradable gel by causing a crosslinking reaction only by mixing with a polymer compound without using radical polymerization (PTL 1). However, this gel absorbs a solvent and dissolves, and an intended structure may not be constructed in some cases. Furthermore, the strength of the gel is low, and there is a problem in that production of a complex three-dimensional structure by which a biological structure is reproduced is difficult.

The inventors of the present invention have found that by increasing the number of branches of the photocleavable crosslinker, it is possible to increase the strength of the gel, and by using the crosslinker, it is possible to form a photodegradable gel which has water content and appropriate water solubility as a cell carrier, and also has the strength that enables construction of a complex and fine three-dimensional structure, and therefore have previously filed the patent application (PTLs 2 and 3 and NPL 6).

CITATION LIST

Patent Literature

[PTL 1] Japanese Unexamined Patent Application, First Publication No. 2012-080844
[PTL 2] Japanese Unexamined Patent Application, First Publication No. 2014-226088
[PTL 3] WIPO Publication No. 2014/188911 A1

Non-Patent Literature

[NPL 1] C. B. Hutson, J. W. Nichol, H. Aubin, H. Bae, S. Yamanlar, S. Al-Haque, S. T. Koshy and A. Khademhosseini, "Synthesis and characterization of tunable poly (ethylene glycol): Gelatin methacrylate composite hydrogels", Tissue Engineering Part A, 17, 1713-1723 (2011).
[NPL 2] L. Schukur, P. Zorlutuna, J. M. Cha, H. Bae and A. Khademhosseini, "Directed differentiation of size-controlled embryoid bodies towards endothelial and cardiac lineages in rgd-modified poly(ethylene glycol) hydrogels", Adv. Healthc. Mat., 2, 195-205 (2013). [NPL 3] Tamura, M. et al. Optical cell separation from three-dimensional environment in photodegradable hydrogels for pure culture techniques. Sci. Rep. 4, 4793 (2014)
[NPL 4] Tibbitt, M. W., Kloxin, A. M., Dyamenahalli, K. U. & Anseth, K. S. Controlled two-photon photodegradation of PEG hydrogels to study and manipulate subcellular interactions on soft materials. Soft Matter 6, 5100-5108 (2010).
[NPL 5] Kloxin, A. M. et al., Science (2009) Vol. 324, pp. 59-63.
[NPL 6] Yanagawa, F. et al. Activated-Ester-Type Photocleavable Crosslinker for Preparation of Photodegradable Hydrogels Using a Two-Component Mixing Reaction. Adv. Healthc. Mat., in press, doi:10.1002/adhm.201400180 (2014).
[NPL 7] DeForest, C. A. & Anseth, K. S. Cytocompatible click-based hydrogels with dynamically tunable properties through orthogonal photoconjugation and photocleavage reactions. Nature Chem. 3, 925-931 (2011).
[NPL 8] Azagarsamy, M. A. & Anseth, K. S. Bioorthogonal Click Chemistry: An Indispensable Tool to Create Multifaceted Cell Culture Scaffolds. Acs Macro Letters 2, 5-9, doi:10.1021/mz300585q (2013).
[NPL 9] Miedel, M. C., Hulmes, J. D. & Pan, Y. C. E. The Use of Fluorescamine as a Detection Reagent in Protein Microcharacterization. J. Biochem. Biophys. Methods 18, 37-52 (1989).
[NPL 10] Ninan, G, Joseph, J. & Abubacker, Z. Physical, Mechanical, and Barrier Properties of Carp and Mammalian Skin Gelatin Films. J. Food Sci. 75, E620-E626, (2010).
[NPL 11] K. Kikuchi, K. Sumaru, J. Edahiro, Y. Ooshima, S. Sugiura, T. Takagi, T. Kanamori, Biotechnol. Bioeng. 103, 552-561 (2009).

SUMMARY OF INVENTION

Technical Problem

In a case where cells are embedded in a photodegradable gel to be cultured for tissue engineering research and in a case where cells are separated by embedding cells in a photodegradable gel, it is important to embed the cells while maintaining the survival rate. However, in the related art described above, a radical polymerization reaction or an amide condensation reaction is used in production of a gel so that cells are allowed to coexist during the reaction, and therefore the cells are embedded in a photodegradable gel. But it is known that these reactions cause cytotoxicity. When a gel is prepared by these methods, it is only possible to embed the cells under a specific condition to maintain the survival rate.

In NPL 7, a method for preparing a photodegradable gel by using a click reaction with low cytotoxicity has been reported. But a gel produced by this method consists of a polyethylene glycol and a polypeptide having no cell adhesiveness. In order to add cell adhesiveness, a cell adhesion RGD group is separately introduced into the polypeptide by an olefin-thiol coupling reaction. As described above, the method of NPL 7 requires a two-step process of formation of a gel by a click reaction and an olefin-thiol coupling reaction using a radical to obtain a cell adhesion photodegradable gel, which is complicated. Furthermore, the interaction between a cell and an extracellular matrix is unclear in general and a case where a functional group to be introduced for imparting appropriate cell adhesiveness is not clear occurs frequently. In such a case, a photodegradable gel containing, as a main component, a protein constituting an extracellular matrix is desoreble.

An object of the present invention is to provide a method for preparing a photodegradable gel in which cells can be embedded in a photodegradable gel without causing cytotoxicity when cells are embedded in a photodegradable gel by allowing cells to coexist at the time of preparation of a photodegradable gel, and which contains a protein as one of the main components; and a photocleavable crosslinker and a chemically modified protein used in the method.

Solution to Problem

The inventors of the present invention have found that dibenzocyclooctyne-terminated photocleavable tetraarm-polyethylene glycol (DBCO-PC-4arm PEG) can be newly synthesized as a photocleavable crosslinker and react with azide-modified gelatin by which a click reaction is generated between a DBCO group and an azido group, and therefore a cell adhesive photodegradable gel can be prepared by a one-stage reaction, and that cytotoxicity does not occur in the click reaction even when allowing the cells to coexist, and have checked that a light irradiation site can specifically degrade by irradiating the photodegradable gel with light, and therefore have solved the above problems.

A molecular structure of DBCO-PC-4armPEG is shown in FIG. 1A. This DBCO-PC-4armPEG has the following characteristics.

(1) DBCO-PC-4ArmPEG has polyfunctional polyethylene glycol (4arm PEG; molecular weight of around 10,000) as a basic skeleton, by which DBCO-PC-4armPEG becomes relatively easy to be compatible with water.

(2) DBCO-PC-4armPEG has four o-nitrobenzyl groups having photocleavable properties in the molecules.

(3) DBCO-PC-4armPEG has four dibenzocyclooctyne (DBCO) groups capable of undergoing a click reaction with an azido group at a molecular terminal.

When DBCO-PC-4arm PEG is mixed with a polymer modified with an azido group, the DBCO group click crosslinking-reacts with the azido group, and therefore a plurality of polymers are crosslinked via DBCO-PC-4arm PEG to gelate (FIG. 1B). The formed crosslinking can be photocleaved (FIG. 1C) by cleavage of the o-nitrobenzyl group moiety in the DBCO-PC-4arm PEG molecule by light irradiation (Example 4), whereby the gel degrades.

Therefore, it is possible to form a gel simply by mixing "an aqueous solution of the photocleavable crosslinker of a cross-linking-type" and "a solution of a polymer having an azido group" (Example 5), or the gel is dissolved by light irradiation (Example 6) (FIG. 1D).

The click crosslinking-type photocleavable crosslinker (a compound A constituting a photodegradable hydrogel to be described later) usable in the present embodiment is not limited to the above DBCO-PC-4armPEG, but is required to have the above three characteristics of (1) water-solubility of a basic skeleton, (2) a plurality of photocleavable groups, and (3) a plurality of groups which undergo click crosslinking reaction with an azido group. (1) The water-solubility of a basic skeleton means that the crosslinker can be dissolved in water or a near-neutral buffer at a temperature of room temperature to 0° C. by 10% by mass or more. Specific water solubility can be determined by visually examining whether a compound which is a basic skeleton or the compound A containing a basic skeleton is dispersed to be dissolved in an interference liquid (pH 7.0 to 7.6) such as a HEPES buffer at a concentration of about 1 to 100 mg/mL. Specifically, as a structure of the water-soluble basic skeleton, a part of the basic skeleton may be substituted with a water-soluble group, and the like. (2) Having the photocleavable groups means that a structure in which molecules can be cleaved or dissociated by the energy of light is contained. A known photodegradable group of the related art can be used as such a photocleavable group and examples thereof include a photodegradable benzyl group. In the present embodiment, a nitrobenzyl group is used. (3) The click crosslinking reaction with an azido group means a group capable of easily and specifically crosslinking through reaction with an azido group. Particularly, there is condensation of an azido group with alkyne. In the present embodiment, specifically, cycloalkyne or azacycloalkyne, and the like have such properties, and in the present embodiment, there is a structure having a cyclooctyne ring or an azacyclooctyne ring.

For example, if a photocleavable crosslinker is characterized to contain a main chain consisting of a linear type- or a branched type- (of three or more branches) polyethylene glycol structure, a photodegradable nitrobenzyl group disposed at both terminals or a branched terminal of the main chain, and a group such as a dibenzocyclooctyne group which can undergo click reaction with an azido group and is disposed at a terminal side of the nitrobenzyl group, this photocleavable crosslinker can be used in the present embodiment as a photocleavable crosslinker having such characteristics. The number of branches of the main chain may be 4 branches or 8 branches. The main chain may be a main chain having a neopentyl skeleton. Specifically, examples of such a compound include a compound of General Formula (1).

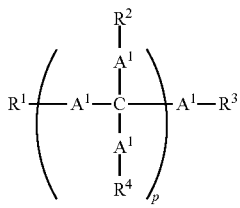
(1)

In General Formula (1), $R^1$ to $R^4$ each independently represents a hydrogen atom, an $-L^1-Z^1-L^2-Z^2$ group, an $-(CH_2CH_2O)_n-L^1-Z^1-L^2-Z^2$ group, or a linear or branched alkyl group having 1 to 20 carbon atoms.

A plurality of $A^1$ represent a linking group, each independently represents a single bond, or a linear or branched alkylene group having 1 to 20 carbon atoms.

One or non-adjacent two or more of $-CH_2-$ in the alkylene group each independently may be substituted by $-CH=CH-$, $-C\equiv C-$, $-O-$, $-CO-$, $-COO-$, $-OCO-$, or a cyclohexylene group. The number of $-CH_2-$ may be 2 to 50.

The symbol p represents an integer of 0 or 1 or more, and a plurality of $R^2$ and $R^4$ may be the same or different from each other. The symbol p may be 0 to 50.

Among $R^1$ to $R^4$, at least two, preferably three or more of Rs contain the $-L^1-Z^1-L^2-Z^2$ group, and two or more Rs are preferably the $-O(CH_2CH_2O)_n-L^1-Z^1-L^2-Z^2$ group. When R contains three or more $-L^1-Z^1-L^2-Z^2$ groups, a crosslinking point per molecule of a crosslinker formed between a photocleavable crosslinker and a polymer compound becomes sufficiently large, and therefore it is possible to increase the strength of the photodegradable gel formed.

The average number of repeating ethylene glycol, n, is within the range of 20 to 500, more preferably within the range of 30 to 250, and still more preferably within the range of 40 to 125. By setting the number of repeating ethylene glycol units within the above range, it is possible to increase the solubility of the gel in water, and it is possible to obtain a photodegradable gel which is easy to handle and has a uniform state when being produced and used. The above average number of repeating ethylene glycol units can be estimated by measuring a molecular weight by gel filtration chromatography or mass spectrometry and estimating the number of the $R^1$ to $R^4$ groups by NMR.

$Z^1$ represents a photodegradable benzyl group, and the benzyl group has an $-L^2-Z^2$ group and one or a plurality of nitro groups on a benzene ring. It is preferable that the number of the nitro groups be 1 or 2. Such a benzyl group is preferably a group represented by General Formula (2) or (3).

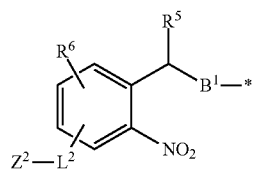
(2)

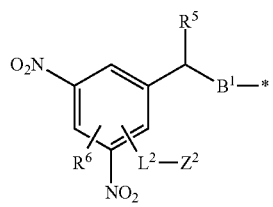
(3)

In General Formulas (2) and (3), $B^1$ represents a group represented by $-B^2-C(=O)-(CH_2)_m-$, $B^2$ represents $-NH-$ or $-O-$, and m represents an integer of 0 to 5 of which 5 is preferable. * represents the position bonding to an oxygen atom of ethylene glycol via $L^1$. $R^5$ represents a hydrogen atom or a linear or branched alkyl group having 1 to 6 carbon atoms, a linear alkyl group having 1 to 6 carbon atoms is more preferable, and a methyl group is particularly preferable. $R^6$ represents a linear or branched alkyl group having 1 to 6 carbon atoms or represents a linear or branched alkoxy group having 1 to 6 carbon atoms, a linear alkoxy group having 1 to 6 carbon atoms is more preferable, and a methoxy group is particularly preferable.

$L^1$ represents a single bond or a linker introduced according to a reaction form in which the compounds of General Formulas (2) and (3) bond to ethylene glycol or $A^1$. Examples of $L^1$ include an ester bond, an ether bond, an amide bond, a carbonyl group, a thioester bond, or a carbamate bond, a alkyl group, and the like, and combinations thereof.

$Z^2$ represents a group having a cyclooctyne ring or an azacyclooctyne ring. An alkyne group in the cyclooctyne ring and the azocyclooctyne ring has high reactivity to an azido group and can click-react with the azido group without using a catalyst such as a copper catalyst. As a group having such a cyclooctyne ring or an azacyclooctyne ring, groups represented by General Formulas (4) to (7) are preferable.

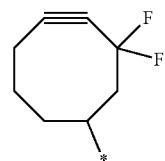

(4)

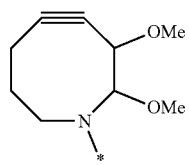

(5)

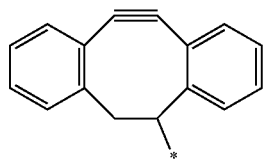

(6)

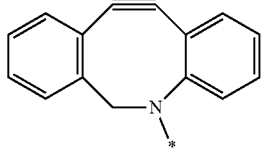

(7)

In General Formulas (4) to (7), * represents a bonding position with a linker group $L^2$. F in the formulas represents a fluorine atom and Me represents a methyl group.

$L^2$ is a linker linking a $Z^2$ group and a $Z^1$ group. For example, in DBCO-PC-4arm PEG used in the examples of the present application, a portion represented by Formula (8) corresponds to $L^2$.

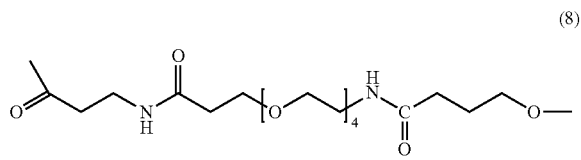

(8)

The structure of Formula (8) is determined based on raw material compounds having the structure of the $Z^1$ group and the structure of the $Z^2$ group, respectively, which are used for linking the $Z^1$ group and the $Z^2$ group, and the reaction form used for linking the raw material compounds thereof. For example, CO— side of Formula (8) may be bonded to * of the $Z^1$ group and O— side may be bonded to * of the $Z^2$ group, or CO— side of Formula (8) may be bonded to * of the $Z^1$ group and O— Side may be bonded to the * of the $Z^2$ group. These raw material compounds and the reaction form are selected from the viewpoint of availability of the raw material compounds and ease of the reaction, and from this viewpoint, as long as the structure of $L^2$ is a structure suitable for linking the $Z^1$ group and the $Z^2$ group, the structure is not limited to the structure of Formula (8). The same applies to $L^1$ described above.

As the compound represented by General Formula (1), more specifically, there are compounds of General Formulas (9) to (11) as preferable compounds. In General Formulas (9) to (11), various parameters have the same meanings as those described above.

(9)

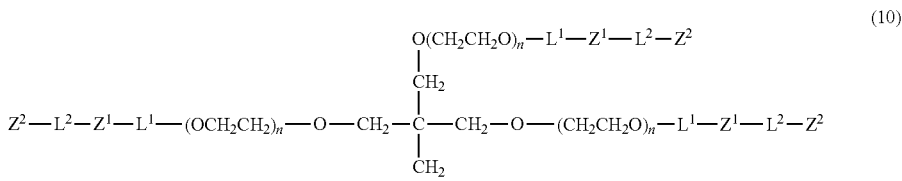

(10)

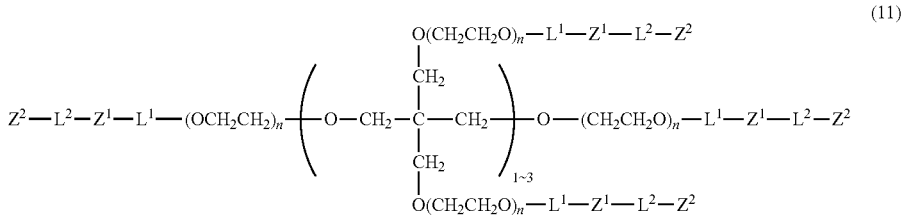

(11)

Regarding evaluation on photocleavability of the click-type photocleavable crosslinker of the present embodiment, the photocleavage reaction can be evaluated by changes in the absorption spectrum before and after light irradiation, for example. The crosslinker of the present embodiment is prepared as an aqueous buffer such as HEPES, the solution in the Eppendorf tube is irradiated with ultraviolet light having a wavelength of 365 nm emitted from an ultraviolet light source through a long wavelength cut filter and a short wavelength cut filter, and therefore the photocleavability of the click-type photocleavable crosslinker of the present embodiment can be evaluated. The absorption spectrum can be measured with an absorption photometer. Furthermore, the measurement can be measured in the range of 300 nm to 700 nm.

(Photodegradable Hydrogel)

In the photodegradable hydrogel of the present embodiment, the above photocleavable crosslinker (compound A) is modified with an azide-modified polymer to be described below, preferably an azide-modified protein (compound B) through an azido group of the compound B. Specifically, an alkyne group contained in a cyclooctyne ring or an azacyclooctyne ring of the following compound A is modified with the following compound B through an azido group of the compound B. A modification ratio is preferably 10% to 100% with respect to a total of the alkyne group. Such a photodegradable hydrogel is obtained by, for example, a reaction in which the alkyne group of the photocleavable crosslinker and an azido group of the following azide-modified protein are condensed.

The content of the compound A and the compound B in the photodegradable hydrogel is within a range of 0 to 2.5 mM, respectively, and cell survival rate (cell viability) when the cells are embedded in the photodegradable hydrogel substantially does not decrease. The phrase substantially does not decrease means that the cell survival rate is 80% or more and preferably 90% or more, before and after embedment. But as a guide, it is preferable that the compound A be 0.6 to 2.5 mM and the compound B be 12.5 to 25.0 mg/mL as a molar concentration in the photodegradable hydrogel. The cell viability is measured by calculating the number of viable cells and dead cells (a total of 100 cells or more) per unit volume (0.005 to 0.050 mL) in a gel in which the cells are cultured using a microscope.

The azide-modified protein is a compound in which a main chain is a protein and at least some of an amino group present at lysine and arginine side chains of the main chain and an amino group present at a terminal of the main chain are modified with an azido group. The protein is preferably a protein having a cell adhesion property. The phrase "having a cell adhesion property" means that the protein contains a large amounts of arginine-glycine-aspartic acid (RGD) which is a cell adhesion active site, which is a property that cells adhere easily as an extracellular matrix. Specific examples of such a protein include gelatin, collagen, laminin, or Matrigel, and the like. In the present embodiment, gelatin is preferable as the protein. As the azide-modified protein of the present embodiment, an azide-modified gelatin in which gelatin is modified with azide is preferable. A molecular weight of the azide-modified protein is not particularly limited and may be appropriately selected, but as a guide, the protein of $10^4$ to $10^5$ can be used.

A schematic diagram of a molecular structure of the azide-modified gelatin (hereinafter referred to as azide-gelatin in some cases) is shown in FIG. 1A. In the azide-gelatin, an azido group is introduced into an amino group derived from lysine and arginine of the terminal of gelatin, which is the main chain.

The azide-modified polymer that can be used in the present embodiment is not limited to the above azide-gelatin and any polymer having a plurality of groups into which an azido group is introduced into the molecule can be used in the present embodiment. As such a polymer, cell adhesion proteins such as gelatin, collagen, and laminin, and a cell culture substrate such as Matrigel containing these proteins as a main component are preferable.

The introduction of an azido group into these polymers is performed by a method for introducing an azido group into an amino group in a polymer via a linker using a modification reagent such as Azide-PEG$_4$-NHS shown in Example 1 described later, but is not limited thereto.

Examples of such an azide-modified polymer include azide-modified matrigel (Azide-matrigel) (Example 1). In Azide-matrigel, an azido group is introduced into an amino group derived from lysine and arginine of a terminal of the molecular chain of a basement membrane component (of which laminin and collagen are the main components according to Corning Incorporated) obtained by dialysis of Matrigel of Corning Incorporated (trade name: Corning Matrigel basement membrane matrix).

By appropriately adjusting the amount of azide-modified reagent used for the polymer, a degree of azide-modification of the polymer can be adjusted. For example, regarding Azide-gelatin and Azide-matrigel, adjusting the amount of Azide-PEG$_4$-NHS used for gelatin and Matrigel as shown in Table 1 and Table 2 to be described later enables adjustment of an introduction ratio of an azido group within a range of 10% to 100% as a modification ratio of the number of amino groups in gelatin and Matrigel.

The water solubility of a plurality of polymers is improved by the introduction of an azido group (Example 2), whereby a crosslinking reaction with the photocleavable crosslinker of a click crosslinking type can be performed by a simple method of mixing both aqueous solutions.

For example, it is possible to prepare the photodegradable gel in a reaction time of several minutes to several tens of minutes at room temperature by mixing an aqueous solution of DBCO-PC-4arm PEG and an aqueous solution of Azide-gelatin or Azide-matrigel (Example 5 and FIG. 4). Whether the formation of the gel by the click reaction is effectively carried out can be checked by a known method of the related art for checking sol-gel transition, for example by rheology measurement. In the present embodiment, it is possible to measure a storage modulus (G') and a loss modulus (G") by using a rheometer to check that gelation occurs when G' exceeds G". Regarding the measurement, when measuring gelation of the photodegradable hydrogel consisting of the above Azide-Gelatin and DBCO-PC-4armPEG, it is preferable that these compounds be mixed in equal amounts so that the concentration of DBCO-PC-4arm PEG becomes 0.6 to 2.3 mM and Azide-gelatin becomes 12.5 to 25.0 mg/mL, and measurement be performed for 1 hour at an interval of 30 seconds under constant temperature condition at 25° C. using a mixed solution of 0.5 mL. In the photodegradable hydrogel of the present embodiment, it is preferable that G' be within a range of 0.01 to 1000 Pa and G" be within a range of 0.01 to 100.

The photodegradable hydrogel of the present embodiment may contain other components used for cell culture. For example, components contained in a cell culture medium may be contained. In addition, a cell growth factor suitable for growth of a target cell may be contained. Examples of the cell growth factor include various growth factors such as transforming growth factor (TG), epithelial cell growth factor (EGF), insulin-like growth factor (IGF), or fibroblast cell growth factor (FGF). The content of the cell growth factor can be 0% to 10% by mass per total mass of the photodegradable hydrogel.

The click-type reaction employed in the present embodiment does not cause cytotoxicity in the cells present in a system upon reaction (Example 7).

On the other hand, it is known that a radical polymerization method and an amide condensation method employed in the related art for preparing a gel cause cytotoxicity in a case where the cells are allowed to coexist. In addition, also in a gelation method using an active ester-type crosslinker having an N-hydroxysuccinimide derivative group as a group forming a crosslink with a hydroxy group or an amino group on a polymer, which is a method used in the prior application (PTLs 1 to 3) by the inventors of the present invention, it is checked that when increasing the crosslinker concentration, cytotoxicity is shown (Example 7).

The above active ester-type crosslinker reacts with various amino groups in an aqueous solution in principle. On the other hand, regarding the reaction between the DBCO group and the azido group used in the click-type crosslinker of the present embodiment, it is known that these reactive groups do not exist in biomolecules such as natural proteins, sugars, and nucleic acids, and the reactivity thereof with other functional groups is low (NPL 8).

That is, in a state where a physiologically active substance such as a medium component or a cell growth factor is mixed in advance, the active ester-type crosslinker reacts not only with an amino group of a polymer forming a gel but also with an amino group of a medium component and the like when forming a hydrogel. On the other hand, in a case of the click-type crosslinker of the present embodiment, even in a state where a physiologically active substance such as a medium component or a cell growth factor is mixed in advance, the crosslinker reacts only with an azido group of a polymer forming a gel with the crosslinker by which undesirable side reactions can be avoided. Therefore, there is an advantage that various physiologically active factors can be mixed in the hydrogel in advance.

For example, even if Matrigel that is not azide-modified is added to a system in which a gel is formed using the click-type photocleavable crosslinker of the present embodiment and Azide-gelatin, a hydrogel is formed in the same manner as in a system to which the above Matrigel is not added (Example 5), and the gel degrades by light irradiation (Example 6).

On the other hand, when forming a hydrogel using the active ester-type crosslinker, it is checked that a hydrogel can not be formed in a case where Matrigel is added at the same concentration. It is considered that this is because when forming a hydrogel, an active ester group reacts with an amino group which is a component such as a protein or an amino acid contained in Matrigel, by which the crosslinking reaction required for forming a hydrogel is inhibited, and therefore a hydrogel can not be formed.

DU145 cells and HeLa cells are embedded in four kinds of hydrogels (Table 7), which are PD-gelatin (25)_M+, PD-gelatin (50)_M+, PD-gelatin (75)_M+, and PD-gelatin (100)_M+ (the above PD refers to polydextrose and M+ refers to a metal element) formed by adding Matrigel, and in the click-type photocleavable crosslinker of the present embodiment, and a cell survival rate is evaluated. As a result, a high level of cell growth is checked in any cell in a wide concentration range of the crosslinker. Therefore, it is checked that the click-type photocleavable crosslinker of the present embodiment is an excellent crosslinker by which cytotoxicity occurs less even in a composition to which Matrigel is added (Example 7 and FIG. 7B). Similarly, it is checked that in a Matrigel-added hydrogel formed by the same method, more remarkable cell growth is exhibited as compared to a no Matrigel-added hydrogel (Example 8 and FIG. 8A and FIG. 8B).

A gel preparation method using a click reaction in the same manner as the present embodiment is reported in NPL 7, but in this method, (1) a cell adhesion function is imparted after "forming a photodegradable gel from 'a click crosslinking-type crosslinker' and 'a photodegradable polypeptide of cell non-adhesive low molecular weight-type'", and therefore, (2) a cell adhesion RGD (Arg-Gly-Asp) group is introduced by using "a radical coupling reaction of 'an intra-polypeptide olefin group (—C═C)' and 'a thiol group (—SH) contained in a cell adhesion substance'". That is, the method of NPL 7 includes a two-step process of formation of a gel by a click reaction and an olefin-thiol coupling reaction using a radical to obtain a cell adhesion photodegradable gel, which is complicated. It is required that these two reactions be performed in the presence of cells to embed the cells in this gel. Moreover, a cell growth rate in the obtained three-dimensional culture was lower than that in the present embodiment. For example, in FIG. 6c of NPL 7, the cells grew remarkably in a region where a gel degraded, but the cells did not grow in the gel. On the other hand, in a system in which Matrigel was added to the photodegradable gel consisting of azide-modified gelatin and DBCO-PC-4armPEG of the present embodiment, it was observed that the cells embedded in a wide concentration range of the crosslinker exhibited a high level of growth (Example 7 and FIG. 7B).

(Culture Device)

The photodegradable hydrogel of the present embodiment can also be used for a culture device. For example, the photodegradable hydrogel of the present embodiment can be used for a culture vessel in which the hydrogel is formed on a bottom surface of the vessel. As the culture vessel, any one of dishes, plates, or flasks which are known in the related art can be used. The term bottom surface refers to a surface on the inside of the culture vessel and any one of the planes of the vessel. As a method for manufacturing the culture device, there is a method for forming the above photodegradable hydrogel on the bottom surface of the vessel, and it is possible to use a known coating means of the related art such as a method in which an aqueous solution in which the photodegradable hydrogel is dissolved is disposed (applied) on the bottom of the vessel and then dried, thereby the photodegradable hydrogel is coated on the bottom surface. In the present embodiment, the compounds A and B are dissolved in a buffer so as to become 25 to 200 mg/mL as a guide. For example, it is preferable that Azide-gelatin and DBCO-PC-4arm PEG be dissolved in a HEPES buffer (pH 7 to 8) so as to become 25 to 400 mg/mL and 0.5 to 40 mM, respectively. The solutions of the compounds A and B are mixed, the culture vessel is filled with the solution so that a thickness becomes about 50 to 1000 μm and incubated at about room temperature (approximately 18 to 30° C.) for about 0.25 to 6 hours to form a gel in the culture vessel. In addition, the cells can be introduced by using a method of embedment culture or sandwich-embedment culture in the culture device. A preferred introduction amount of cells is $10^3$ to $10^7$ cells/mL per volume of the photodegradable hydrogel.

(Method for Forming Tissue)

The photodegradable hydrogel of the present embodiment can also be used for a method for forming tissue. For example, the photodegradable gel can be used to perform the method for forming tissue including the following steps:

(I) a step of forming the photodegradable hydrogel in which cells are embedded;

(II) a step of defining a structure of the photodegradable hydrogel by light irradiation; and (III) a step of culturing the cells to form tissue.

In the step (I) of forming the photodegradable hydrogel in which cells are embedded, firstly the compounds A and B are dissolved in a buffer, respectively. In the present embodiment, it is preferable that azide-modified gelatin (Azide-gelatin) and DBCO-PC-4armPEG be dissolved in a HEPES buffer (pH 7 to 8) as the compound A so as to become 25 to 400 mg/mL and 0.5 to 40 mM, respectively. The cultured cells are dispersed in the solution of the compound B among the solutions at a concentration of $10^3$ to $10^7$ cells/mL as a guide. In the present embodiment, the cell culture solution is dispersed at a concentration of 0.5 to $3.0 \times 10^5$ cells/mL. Next, the buffer of the compound A is added to the solution of the compound B in which the cells are dispersed to prepare a gel. In the present embodiment, equal amounts of the solutions of the compounds A and B are mixed, a vessel is formed using a spacer to prepare a gel, the mixed solution is prepare so that a thickness becomes 50 to 300 μm and incubated for about 0.25 to 6 hours to prepare the photodegradable hydrogel.

In the step (II) of defining a structure of the photodegradable hydrogel, the light irradiation is performed by emitting light having the energy of 0.25 to 3.0 J, specifically, light intensity of 40 to 350 mW/cm² for 1 to 75 seconds so that the photodegradable hydrogel degrades. By emitting light under the above conditions, it is possible to degrade the photodegradable hydrogel to form a gel structure according to a micropattern while minimizing cell death. Thereafter, the structure of the photodegradable hydrogel is specified by 0.01% Coomassie Brilliant Blue. When specifying the structure of the photodegradable hydrogel, in the present embodiment, the structure of the photodegradable hydrogel is observed with a microscope and a site on the structure of the hydrogel which is irradiated with light, that is, the degrading state is observed from the micropattern formed in the photodegradable hydrogel.

In the step (III) of culturing the cells to form tissue, a culture medium suitable for the cells is added to the photodegradable hydrogel and cell culture is performed at optimum temperature and time depending on the cells. For example, a culture medium such as DMEM is preferably used for HeLa cells and DU145 cells of the present embodiment and culture is performed at 35° C. to 39° C. (most preferably around 37° C.) for 12 to 48 hours (most preferably around 24 hours).

(Method for Separating Cells)

The photodegradable hydrogel of the present embodiment can also be used for a method for separating cells. For example, the photodegradable gel can be used to perform the method for separating cells including the following steps:

(I) a step of forming the photodegradable hydrogel in which cells are embedded;

(II) a step of dissolving the photodegradable hydrogel in a region containing a specific cell among the cells by light irradiation; and (III) a step of washing the dissolved photodegradable hydrogel to recover the specific cell in the dissolved region.

In the step (I) of forming the photodegradable hydrogel in which cells are embedded, firstly the compounds A and B are dissolved in a buffer, respectively. In the present embodiment, it is preferable that azide-modified gelatin (Azide-gelatin) and DBCO-PC-4armPEG be dissolved in a HEPES buffer (pH 7 to 8) as the compound A so as to become 12.5 to 50 mg/mL and 0.5 to 5.0 mM, respectively. The cultured cells are dispersed in the solution of the compound B among the solutions at a concentration of $10^3$ to $10^7$ cells/mL as a guide. In the present embodiment, the cell culture solution is dispersed at a concentration of 0.5 to $3.0 \times 10^5$ cells/mL. Next, the buffer of the compound A is added to the solution of the compound B in which the cells are dispersed to prepare a gel. In the present embodiment, equal amounts of the solutions of the compounds A and B are mixed, a vessel is formed using a spacer to prepare a gel, the mixed solution is prepared so that a thickness becomes 50 to 300 μm and incubated for about 0.25 to 6 hours to prepare the photodegradable hydrogel.

In the step (II) of dissolving the photodegradable hydrogel, the light irradiation is performed by emitting light having the energy of 0.25 to 3.0 J, specifically, light intensity of 40 to 350 mW/cm² for 1 to 75 seconds so that the photodegradable hydrogel degrades. By emitting light under the above conditions, it is possible to degrade (dissolve) the photodegradable hydrogel to form a gel structure according to a micropattern without cell death.

In the step (III) of recovering the specific cell in the dissolved region from the dissolved photodegradable hydrogel, the specific cell in the dissolved region is recovered by aspirating the cell culture medium with a pipette, or aspirating after 1 to 10 times of pipetting with the cell culture medium.

Specifically, the present application provides the following invention.

<1> A photodegradable hydrogel obtained by condensation of an alkyne group contained in a cyclooctyne ring or an azacyclooctyne ring of the following compound A with an azido group of the compound B.

(compound A)

A photocleavable crosslinker characterized by containing a main chain containing a linear type- or a branched type- (of three or more branches) polyethylene glycol structure, and a photodegradable nitrobenzyl group disposed at both terminals or a branched terminal of the main chain and a group having a cyclooctyne ring or an azacyclooctyne ring disposed at a terminal side of the nitrobenzyl group.

(compound B)

An azide-modified protein characterized in that a main chain is a protein and at least some of an amino group present at lysine and arginine side chains of the main chain and an amino group present at a terminal of the main chain are modified with the azido group.

<2> The photodegradable hydrogel according to <1>, in which the protein of the compound B is a cell adhesion protein such as gelatin, collagen, laminin and Matrigel.

<3> The photodegradable hydrogel according to <1> or <2>, in which the average number of repeating ethylene glycol units in the polyethylene glycol structure of the compound A is within the range of 30 to 250.

<4> The photodegradable hydrogel according to any one of <1> to <3>, in which the number of branches in the branched type-main chain of the compound A is 4 or 8.

<5> The photodegradable hydrogel according to any one of <1> to <4>, in which the branched type-main chain of the compound A has a neopentyl skeleton on the center thereof.

<6> The photodegradable hydrogel according to any one of <1> to <5>, in which the group having a cyclooctyne ring or an azacyclooctyne ring is an azadibenzocyclooctyne (DBCO) group.

<7> The photodegradable hydrogel according to any one of <1> to <6>, in which the photodegradable hydrogel contains a cell growth factor.

<8> A culture device, in which the photodegradable hydrogel according to any one of <1> to <7> is formed on a bottom surface of a culture vessel.

<9> A method for forming tissue using the photodegradable gel according to any one of <1> to <7>, the method including:

(I) a step of forming the photodegradable gel in which cells are embedded;

(II) a step of defining a structure of the gel by light irradiation; and (III) a step of culturing the cells to form tissue.

<10> A method for separating cells using the photodegradable gel according to any one of <1> to <7>, the method including:

(I) a step of forming the photodegradable gel in which cells are embedded;

(II) a step of dissolving the gel in a region containing a specific cell among the cells by light irradiation; and (III) a step of washing the dissolved gel to recover the cell in the dissolved region.

In addition, an embodiment of the present invention has the following aspects.

<1> A photodegradable hydrogel of which an alkyne group contained in a cyclooctyne ring or an azacyclooctyne ring of the following compound A is modified with the following compound B through an azido group of the compound B.

(compound A)

A compound is a photocleavable crosslinker which contains a main chain having a linear type- or a branched type- (of three or more branches) polyethylene glycol structure, a photodegradable nitrobenzyl group disposed at both terminals or a branched terminal of the main chain, and a group having a cyclooctyne ring or an azacyclooctyne ring disposed at a terminal side of the nitrobenzyl group.

(compound B)

A compound is an azide-modified protein, in which a main chain is a protein and at least some of an amino group present at lysine and arginine side chains of the main chain and an amino group present at a terminal of the main chain are modified with the azido group.

<2> The photodegradable hydrogel according to <1>, in which the protein of the compound B includes one or more of cell adhesion proteins selected from gelatin, collagen, laminin and Matrigel.

<3> The photodegradable hydrogel according to <1> or <2>, in which the average number of repeating ethylene glycol units in the polyethylene glycol structure of the compound A is within the range of 30 to 250.

<4> The photodegradable hydrogel according to any one of <1> to <3>, in which the number of branches in the branched type-main chain of the compound A is 4 or 8.

<5> The photodegradable hydrogel according to any one of <1> to <4>, in which the branched type-main chain of the compound A has a neopentyl skeleton on the center thereof.

<6> The photodegradable hydrogel according to any one of <1> to <5>, in which the group having a cyclooctyne ring or an azacyclooctyne ring of the compound A is an azadibenzocyclooctyne (DBCO) group.

<7> The photodegradable hydrogel according to any one of <1> to <7>, in which the photodegradable hydrogel contains a cell growth factor.

<8> The photodegradable hydrogel according to any one of <1> to <8>, in which a modification ratio at which the alkyne group is modified through an azido group is 10% to 100% with respect to the number of the alkyne group.

<9> The photodegradable hydrogel according to any one of <1> to <8>, in which in the compound B, an azido-modification ratio of the amino group in the azide-modified protein is 10% to 100% with respect to the number of the amino group.

<10> A culture device, in which the photodegradable hydrogel according to any one of <1> to <9> is formed on a bottom surface of a culture vessel.

<11> A method for forming tissue using the photodegradable hydrogel according to any one of <1> to <9>, the method including:

(I) a step of forming the photodegradable hydrogel in which cells are embedded;

(II) a step of defining a structure of the photodegradable hydrogel by light irradiation; and (III) a step of culturing the cells to form tissue.

<12> The method for forming tissue according to <11>, in which in the step of defining a structure of the photodegradable hydrogel, light having a wavelength of 300 to 500 nm is emitted in the light irradiation, and a structure of the photodegradable hydrogel is defined by CBB staining, fluorescent staining, or microscopic observation.

<13> A method for separating cells using the photodegradable hydrogel according to any one of <1> to <9>, the method including:

(I) a step of forming the photodegradable hydrogel in which cells are embedded;

(II) a step of dissolving the photodegradable hydrogel in a region containing a specific cell by light irradiation; and (III) a step of washing the dissolved photodegradable hydrogel to recover the cell in the dissolved region.

<14> The method for separating cells according to <13>, in which in the step of dissolving the photodegradable hydrogel, light having a light intensity of 0.005 to 1.0 W/cm$^2$ is emitted in the light irradiation and the photodegradable hydrogel is dissolved by pipetting.

Advantageous Effects of Invention

According to one embodiment of the present invention, when crosslinking a polymer compound using a crosslinker to form a gel, a click crosslinking-type photocleavable crosslinker of the present embodiment is used as a crosslinker, an azide-modified polymer is used as a polymer, and therefore a photodegradable gel can be prepared by a one stage reaction.

The reaction between the click crosslinking-type photocleavable crosslinker of the present embodiment and the azido group on the polymer has less cytotoxicity, and thus the formation of the photodegradable gel can be carried out in the presence of cells. Therefore, it is possible to prepare a gel containing cells that are three-dimensionally dispersed to be embedded inside the prepared gel. The cells in the gel have a high viability and by culturing the cells in the gel, it is possible to obtain a three-dimensional culture of the cells.

The three-dimensional culture of the cells is irradiated with light so that the gel degrades, and therefore three-dimensionally cultured cells can be extracted. By performing light irradiation only at a specific site, it is also possible to extract only cells at the specific site.

The cells embedded in the gel are cultured by using the photodegradable gel in which the click crosslinking-type photocleavable crosslinker of the present embodiment is used, and therefore, tissue mimicking a three-dimensional structure in vivo can be artificially reconstructed, or the cells are appropriately extracted and therefore can be used for more reliable assays and the like.

DESCRIPTION OF EMBODIMENTS

Examples

Figure 1A:
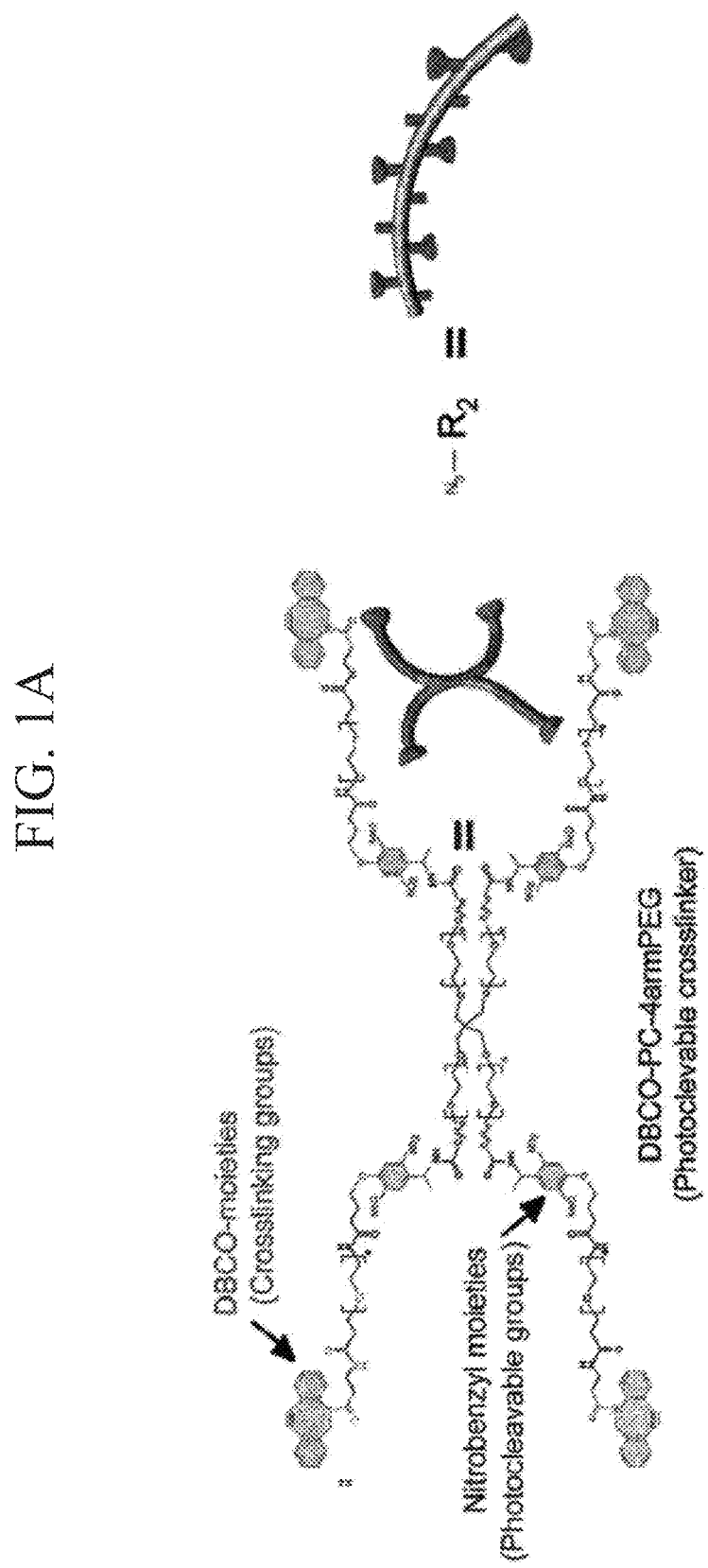
FIG. 1A is a schematic diagram of crosslinking formation and hydrogel formation by click reaction, and degradation by light irradiation, and a schematic diagram of a click crosslinking-type photocleavable crosslinker, which is DBCO-PC-4armPEG, and a molecular structure of an azide-modified gelatin. $R_2$ represents a main chain of the gelatin molecule.
Figure 1B:
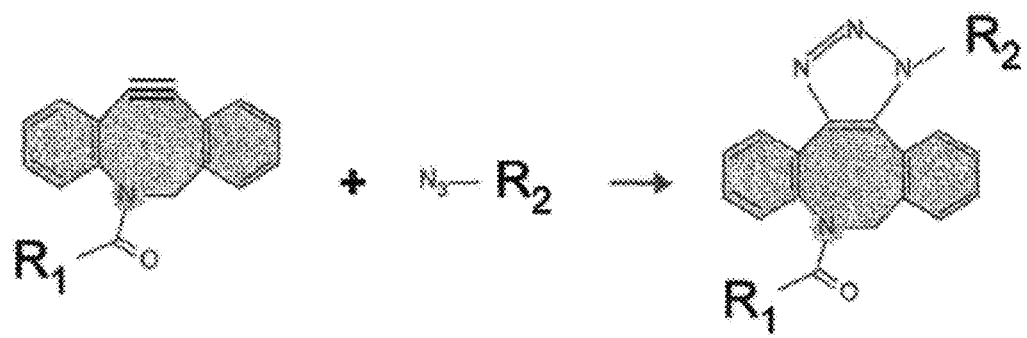
FIG. 1B shows crosslinking formation between DBCO-PC-4armPEG and the azide-modified gelatin by click reaction. $R_1$ represents a site on a main chain side of DBCO-PC-4armPEG.
Figure 1C:
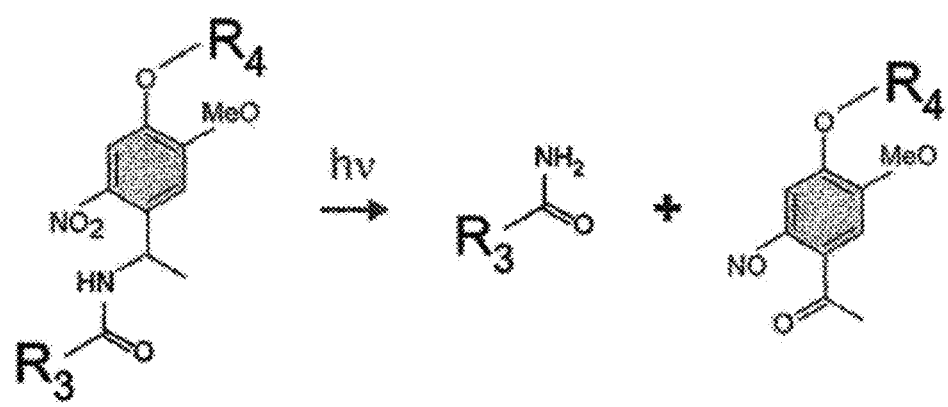
FIG. 1C is a schematic diagram of degradation of a crosslinking site by light irradiation. $R_3$ represents a site derived from the main chain side of DBCO-PC-4armPEG, and $R_4$ represents a site derived from a side chain side of the azide-modified gelatin and DBCO-PC-4armPEG.
Figure 1D:
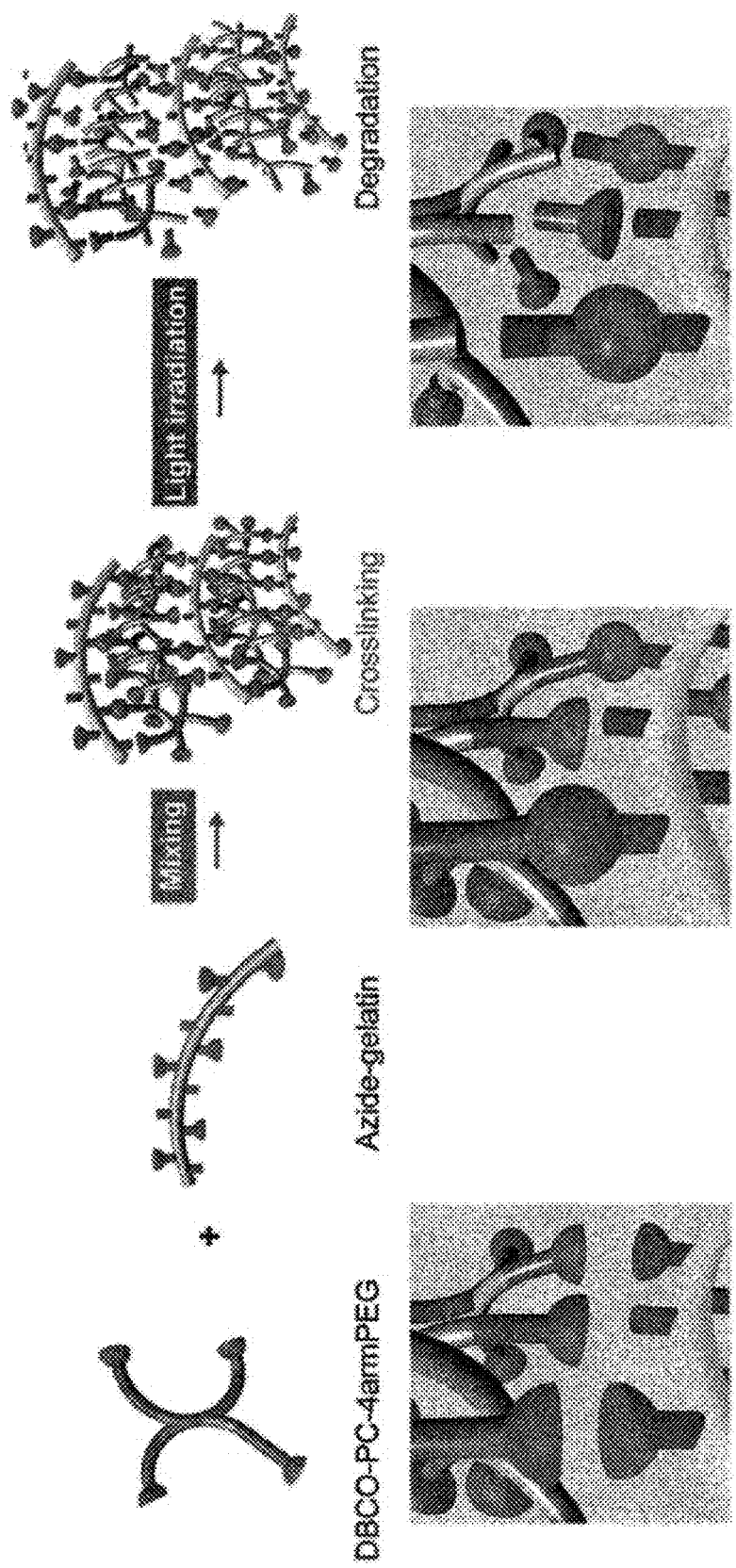
FIG. 1D is a schematic diagram of hydrogel formation by reaction between DBCO-PC-4armPEG and the azide-modified gelatin, and degradation by light irradiation.

Hereinafter, the present embodiment will be described in further detail based on examples, but the present invention is not limited to these examples at all, and it is needless to say that various material changes, design changes, setting adjustments, and the like are possible without departing from the gist of the present invention.

In the following examples, the following materials were used.

Gelatin (G2500, Sigma-Aldrich Co. LLC., St. Louis, Mo.), Azide-PEG$_4$-NHS ester (Click Chemistry Tools LLC. Scottsdale, Ariz.), DBCO-PEG$_4$-amine (Click Chemistry Tools LLC.), DBCO-sulfo-NHS (Click Chemistry Tools LLC.), Matrigel (Corning, Tewksbury, Mass.) were purchased to be used. 4-(2-hydroxyethyl)-1-piperazineethanesulfonic acid (HEPES, Wako Pure Chemical Industries, Ltd., Osaka, Japan) was dissolved in MilliQ water (Millipore, Billerica, USA) at a concentration of 300 mM, and a pH was adjusted to 7.4 with 0.1N sodium hydroxide aqueous solution to prepare a HEPES buffer. The prepared solution was used after being filtrated using a filter having a pore size of 0.2 µm (Millipore Co., Billerica, Mass.).

Example 1. Synthesis of Azide-Modified Gelatin and Azide-Modified Matrigel

According to the following procedure, azide-modified Gelatin and azide-modified matrigel were synthesized to gelate Gelatin and Matrigel by click reaction (Formula 1).

Gelatin is a polymer of which water solubility increases by modifying collagen, which is a cell adhesion protein, with acid, alkali, heat, and the like, and maintains cell adhesiveness while being modified, and therefore is used as a substrate for cell culture as same as collagen. Gelatin is inexpensive compared to collagen, and therefore is frequently used for coating of a culture dish.

Azide-modified gelatin was synthesized by mixing gelatin and Azide-PEG$_4$-NHS ester at a ratio shown in Table 1. A synthesis scheme is shown in Formula 1. Gelatin was dissolved in 300 mM HEPES buffer having a pH 7.4, Azide-PEG$_4$-NHS ester was dissolved in 10 mM phthalic acid buffer (pH 4.0), and these were mixed and stirred at 37° C. for 2 hours. The reaction solution was put in a dialysis membrane (fraction molecular weight 6,000 to 8,000, Spectrum laboratories, Inc., Rancho Domingues, Calif.) and dialyzed against MilliQ water (5 L) for 24 hours. MilliQ water was exchanged a total of five times after 30 minutes, 1, 3, 5, and 7 hours. The dialyzed sample was dried using a freeze dryer (FDS-1000, Tokyo RIKAKIKAI Co., LTD., Tokyo, Japan) to obtain azide-modified gelatin. The yield was between 71% and 82%. The obtained azide-modified gelatin was dissolved in 300 mM HEPES of pH 7.4 at 37° C. and stored at 4° C. The azide-modified amount with respect to a reactive amino group of azide-modified gelatin was quantified by using fluorescamine and using a fluorescent labeling method of a reactive amino group described in NPL 9.

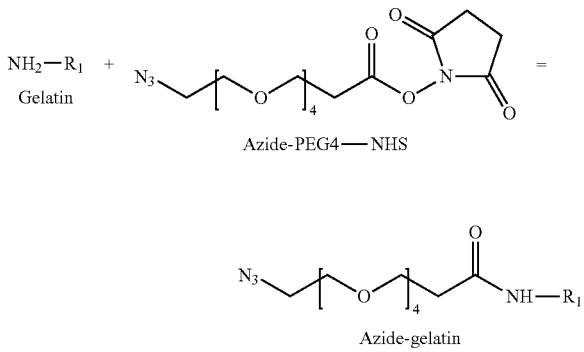

Formula 1. Schematic diagram of synthesis of azide-modified gelatin by reaction of gelatin with Azide-PEG$_4$—NHS

TABLE 1

Mixed concentration of gelatin and Azide-PEG$_4$-NHS when synthesizing azide-modified gelatin

| Type of azide-modified gelatin | Feed concentration when synthesizing | | Ratio$^a$ of azido group to amino group in gelatin Azide/NH$_2$ (mol %)$^a$ | Azidification modification ratio$^b$ of reactive amino group in gelatin (mol %) |
|---|---|---|---|---|
| | Gelatin (mg/mL) | Azide-PEG$_4$-NHS (mM) | | |
| Gelatin | 25 | 0 | 0 | 0 |
| Azide-gelatin (25) | | 4.7 | 25 | 37 |
| Azide-gelatin (50) | | 9.4 | 50 | 67 |
| Azide-gelatin (75) | | 14.1 | 75 | 87 |
| Azide-gelatin (100) | | 18.8 | 100 | 98 |

The content of amino group in $^a$gelatin was calculated based on information of NPL 10.
The $^b$azide-modified amount was quantified using fluorescamine and using the method described in NPL 9.

Matrigel is a cell culture substrate sold by Corning Incorporated, and various growth factors such as transforming growth factor (TG), epithelial cell growth factor (EGF), insulin-like growth factor (IGF), and fibroblast cell growth factor (FGF) are contained in addition to an extracellular matrix such as laminin and collagen which are main components thereof.

When synthesizing azide-modified matrigel, Matrigel was dialyzed and freeze-dried in advance before use in the same protocol as the above protocol. Azide-modified matrigel was synthesized by mixing Matrigel and Azide-PEG$_4$-NHS ester at a ratio shown in Table 2 in the same method as the synthesis of azide-modified gelatin. The yield was between 68% and 93%. The obtained azide-modified matrigel was dissolved in 300 mM HEPES of pH 7.4 and dissolved at 4° C. The dissolved azide-modified matrigel was stored at 4° C. until immediately before being used. The azide-modified amount of azide-modified matrigel with respect to the reactive amino group was quantified by using fluorescamine and using the fluorescent labeling method of the reactive amino group described in NPL 9.

TABLE 2

Mixed concentration of purified Matrigel and Azide-PEG$_4$-NHS when synthesizing azide-modified matrigel

| Type of azide-modified matrigel | Feed concentration when synthesizing | | Ratio[a] of azido group to amino group in matrigel Azide/NH$_2$ (mol %)[a] | Azidification modification ratio[b] of reactive amino group in gelatin (mol %) |
|---|---|---|---|---|
| | Matrigel (mg/mL) | Azide-PEG$_4$-NHS (mM) | | |
| Gelatin | 5 | 0 | 0 | 0 |
| Azide-matrigel (25) | | 3.8 | 25 | 44 |
| Azide-matrigel (50) | | 7.5 | 50 | 67 |
| Azide-matrigel (75) | | 11.3 | 75 | 80 |
| Azide-matrigel (100) | | 15.0 | 100 | 83 |

The content of the amino group in [a]Matrigel was quantified using fluorescamine and using the method described in NPL 9. The reactive amino group of azidified reaction gelatin was comparatively quantified based on information when the gelatin solution was 100 mol % of the reactive amino group and HEPES was 0 mol % of the reactive amino group. The [b]azide-modified amount was quantified using fluorescamine and using the fluorescent labeling method of the reactive amino group described in NPL 9.

Example 2. Examination of Solubility of Azide-Modified Gelatin and Azide-Modified Matrigel The solubility of azide-modified Gelatin and azide-modified matrigel was examined in 300 mM HEPES buffer (pH 7.4) (Table 5 and Table 6). It is known that if 25 mg/mL aqueous solution of gelatin is kept at 4° C. and 25° C., gelation occurs, but the solution dissolves at 37° C. On the other hand, it was checked that when gelatin was azide-modified to become azide-modified gelatin, gelation does not occur even when the 25 mg/mL aqueous solution was kept at 25° C. (Table 5). It is considered that this is because hydrophilicity of gelatin increased by the introduction of an azido group, by which water solubility of gelatin was improved. It can be said that a fact that mixing operation of the solution became possible at room temperature (25° C.) due to this improvement in hydrophilicity is an excellent property when preparing the photodegradable gel.

TABLE 3

Comparison of water solubility of gelatin and azide-modified gelatin. Each was dispersed in 300 mM HEPES buffer (pH 7.4) at a concentration of 25 mg/mL, and the solubility was examined.

| | Gelatin concentration (mg/mL) | Temperature (° C.) | Solubility |
|---|---|---|---|
| Gelatin | 25 | 4 | Insoluble (gelation) |
| | | 25 | Insoluble (gelation) |
| | | 37 | Dissolved |
| Azide-gelatin (25) | | 4 | Insoluble (gelation) |
| | | 25 | Dissolved |
| | | 37 | Dissolved |
| Azide-gelatin (50) | | 4 | Insoluble (gelation) |
| | | 25 | Dissolved |
| | | 37 | Dissolved |

TABLE 3-continued

Comparison of water solubility of gelatin and azide-modified gelatin. Each was dispersed in 300 mM HEPES buffer (pH 7.4) at a concentration of 25 mg/mL, and the solubility was examined.

| | Gelatin concentration (mg/mL) | Temperature (° C.) | Solubility |
|---|---|---|---|
| Azide-gelatin (75) | | 4 | Insoluble (gelation) |
| | | 25 | Dissolved |
| | | 37 | Dissolved |
| Azide-gelatin (100) | | 4 | Insoluble (gelation) |
| | | 25 | Dissolved |
| | | 37 | Dissolved |

It is checked that 25 mg/mL aqueous solution of Matrigel can maintain the dissolution state at 4° C., but if the solution is kept at 25° C., gelation occurs (Table 4). On the other hand, it was checked that when Matrigel was azide-modified to become azide-modified matrigel, gelation does not occur even when the 25 mg/mL aqueous solution was kept at 25° C. (Table 4). It is considered that this is because hydrophilicity of Matrigel increased by the introduction of an azido group, by which water solubility of Matrigel was improved. It can be said that a fact that mixing operation of the solution became possible at room temperature (25° C.) due to this improvement in hydrophilicity is an excellent property when preparing the photodegradable gel.

TABLE 4

Comparison of water solubility of Matrigel and azide-modified matrigel. Each was dispersed in 300 mM HEPES buffer (pH 7.4) at a concentration of 25 mg/mL, and the solubility was examined.

| | Matrigel concentration (mg/mL) | Temperature (° C.) | Solubility |
|---|---|---|---|
| matrigel | 25 | 4 | Dissolved |
| | | 25 | Insoluble (gelation) |
| | | 37 | Insoluble (gelation) |
| Azide-matrigel (25) | | 4 | Dissolved |
| | | 25 | Dissolved |
| Azide-matrigel (50) | | 4 | Dissolved |
| | | 25 | Dissolved |
| Azide-matrigel (75) | | 4 | Dissolved |
| | | 25 | Dissolved |
| Azide-matrigel (100) | | 4 | Dissolved |
| | | 25 | Dissolved |

Comparative Example 1. Synthesis of DBCO-Modified Gelatin and Examination of Water Solubility Thereof Since the click reaction forms a covalent bond by the reaction between a DBCO group and an azido group, it is considered that the DBCO group may be introduced into gelatin and the azido group may be introduced into the crosslinker in order to form a gel using the click reaction. In order to verify the above, the DBCO group was introduced into gelatin to synthesize DBCO-modified gelatin, and water solubility was examined in 300 mM HEPES buffer (pH 7.4).

DBCO-modified gelatin was synthesized by mixing gelatin and DBCO-sulfo-NHS ester at a ratio shown in Table 5. The synthesis scheme is shown in Formula 2. Gelatin was dissolved in 300 mM HEPES buffer of pH 7.4 and DBCO-sulfo-NHS ester solution was dissolved in 10 mM phthalic acid buffer (pH 4.0), and these were mixed and reacted at 37° C. for 2 hours.

Formula 2. Schematic diagram of synthesis of DBCO-modified gelatin by reaction of gelatin with DBCO-sulfo-NHS

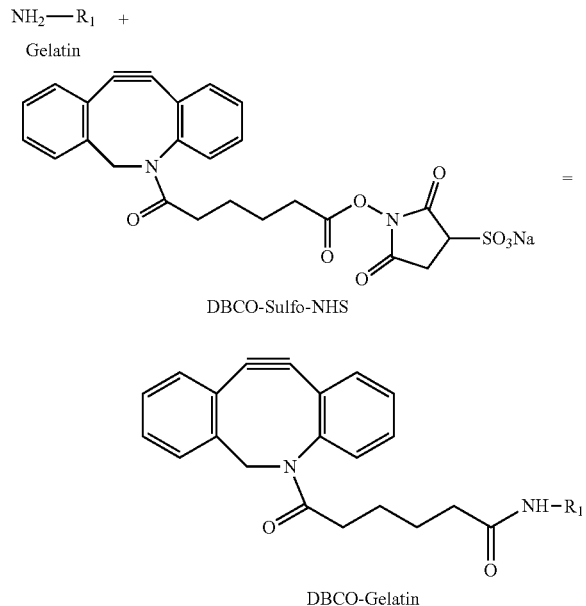

Figure 2:
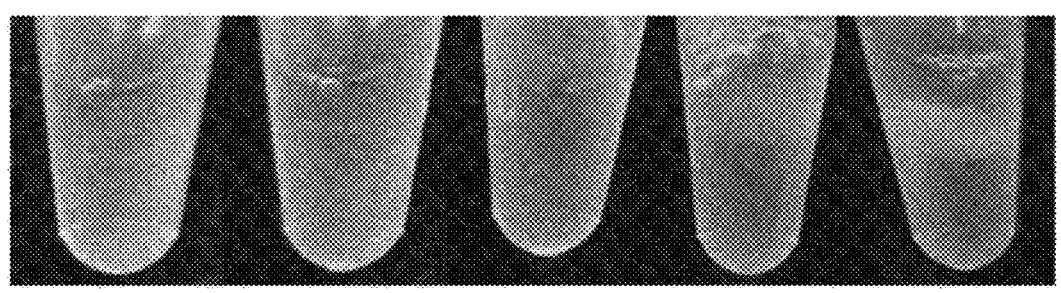
FIG. 2 is a photograph showing the state 2 hours after reacting of gelatin and DBCO-sulfo-NHS at 37° C., which is the state 2 hours after reacting of gelatin, DBCO-gelatin (25), DBCO-gelatin (50), DBCO-gelatin (75), and DBCO-gelatin (100) from the left in order.

As a result of examining the water solubility of the synthesized DBCO-modified gelatin in 300 mM HEPES buffer (pH 7.4), it was checked that in the process of synthesizing DBCO-modified gelatin, there was no condition under which DBCO-modified gelatin can be dissolved at 25° C., and even at 37° C., only DBCO-gelatin (25) having a low introduction ratio of the DBCO group is dissolved (Table 6 and FIG. 2).

From the results, it was checked that azide-modified gelatin and azide-modified matrigel exhibited more high solubility in a HEPES buffer compared to DBCO-modified gelatin, and this is excellent for preparing the photodegradable gel using the click reaction.

TABLE 6

Comparison of water solubility of gelatin and DBCO-modified gelatin. Each was dispersed in 300 mM HEPES buffer (pH 7.4) at a concentration of 25 mg/mL, and the solubility was examined.

| | Gelatin Concentration (mg/mL) | Temperature (° C.) | Solubility |
|---|---|---|---|
| Gelatin | 25 | 4 | Insoluble (gelation) |
| | | 25 | Insoluble (gelation) |
| | | 37 | Dissolved |
| DBCO-gelatin (25) | | 4 | Insoluble (gelation) |
| | | 25 | Insoluble (gelation) |
| | | 37 | Dissolved |
| DBCO-gelatin (50) | | 4 | Insoluble (gelation) |
| | | 25 | Insoluble (gelation) |
| | | 37 | Insoluble (gelation) |
| DBCO-gelatin (75) | | 4 | Insoluble (gelation) |
| | | 25 | Insoluble (gelation) |
| | | 37 | Insoluble (gelation) |
| DBCO-gelatin (100) | | 4 | Insoluble (gelation) |
| | | 25 | Insoluble (gelation) |
| | | 37 | Insoluble (gelation) |

Example 3. Synthesis of DBCO-PC-4ArmPEG

In order to synthesize a click crosslinking-type photocleavable crosslinker, DBCO-PC-4arm PEG, firstly, a pho-

TABLE 5

Mixed concentration of gelatin and DBCO-PEG$_4$-NHS (after mixing) when synthesizing DBCO-modified gelatin

| Type of DBCO-gelatin | Gelation concentration (mg/mL) | DBCO-sulfo-NHS concentration (mM) | Feed amount[a] of DBCO group to amino group in gelatin (DBCO/NH$_2$) (mol %)[a] |
|---|---|---|---|
| Gelatin | 25 | 0 | 0 |
| DBCO-gelatin (25) | | 4.7 | 25 |
| DBCO-gelatin (50) | | 9.4 | 50 |
| DBCO-gelatin (75) | | 14.1 | 75 |
| DBCO-gelatin (100) | | 18.8 | 100 |

The content of amino group in [a]gelatin was calculated based on the information of NPL 10 with a molar mass of amino group contained in gelatin.

tocleavable crosslinker NHS-PC-4arm PEG of an active ester-type was synthesized according to a method for introducing a nitrobenzyl group into an active ester terminal 4arm PEG described in NPL 6.

DBCO-PC-4armPEG was synthesized by reacting NHS-PC-4armPEG with DBCO-PEG$_4$-amine. The synthesis scheme is shown in Formula 3. DBCO-PEG$_4$-amine (600 mg) and NHS-PC-4armPEG (3.018 g) were added to 125 mL of dimethyl sulfoxide (DMSO) and heated at 40° C. and stirred. The reactant was precipitated in diethyl ether to be purified. First, the reaction solution was added dropwise to 1 L of diethyl ether and ice-cooled for 30 minutes. After removing the supernatant by decantation, the precipitate was dissolved in 10 mL of THF. Next, the reactant dissolved in THF was added dropwise to 400 mL of diethyl ether to obtain a precipitate. This ether precipitation was repeated three times to obtain 3.4 g of DBCO-PC-4armPEG (yield: 99%).

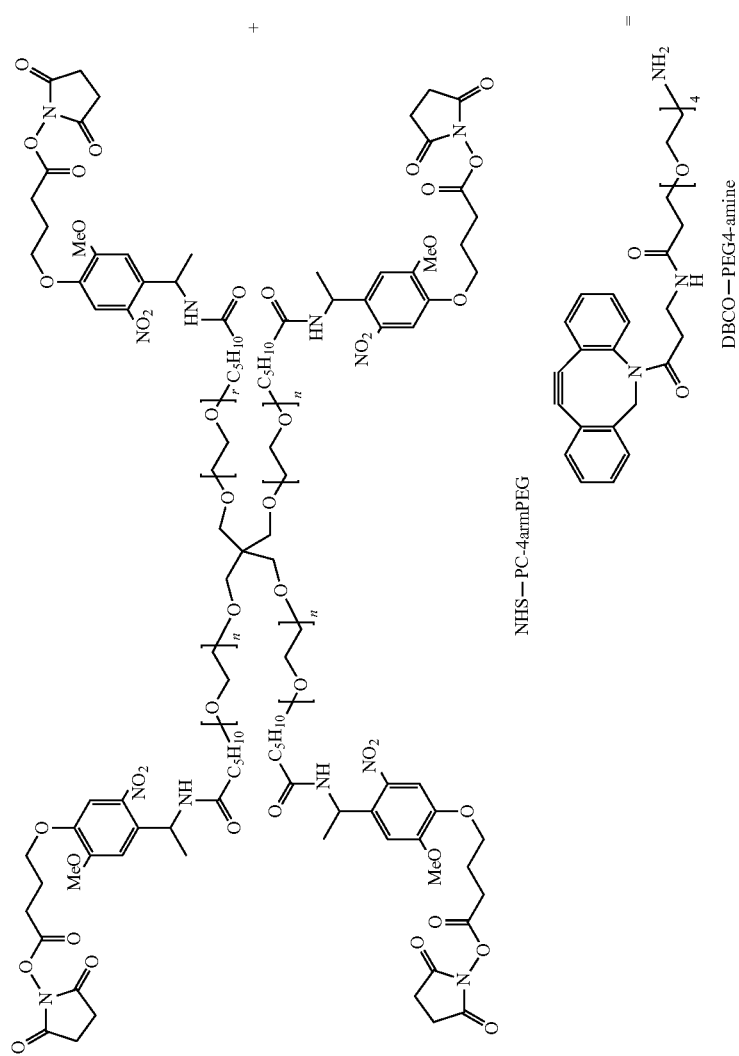
Formula 3. Schematic diagram of synthesis of DBCO—PC-4armPEG by reaction of NHS—PC-4armPEG with DBCO—PEG$_4$-amine

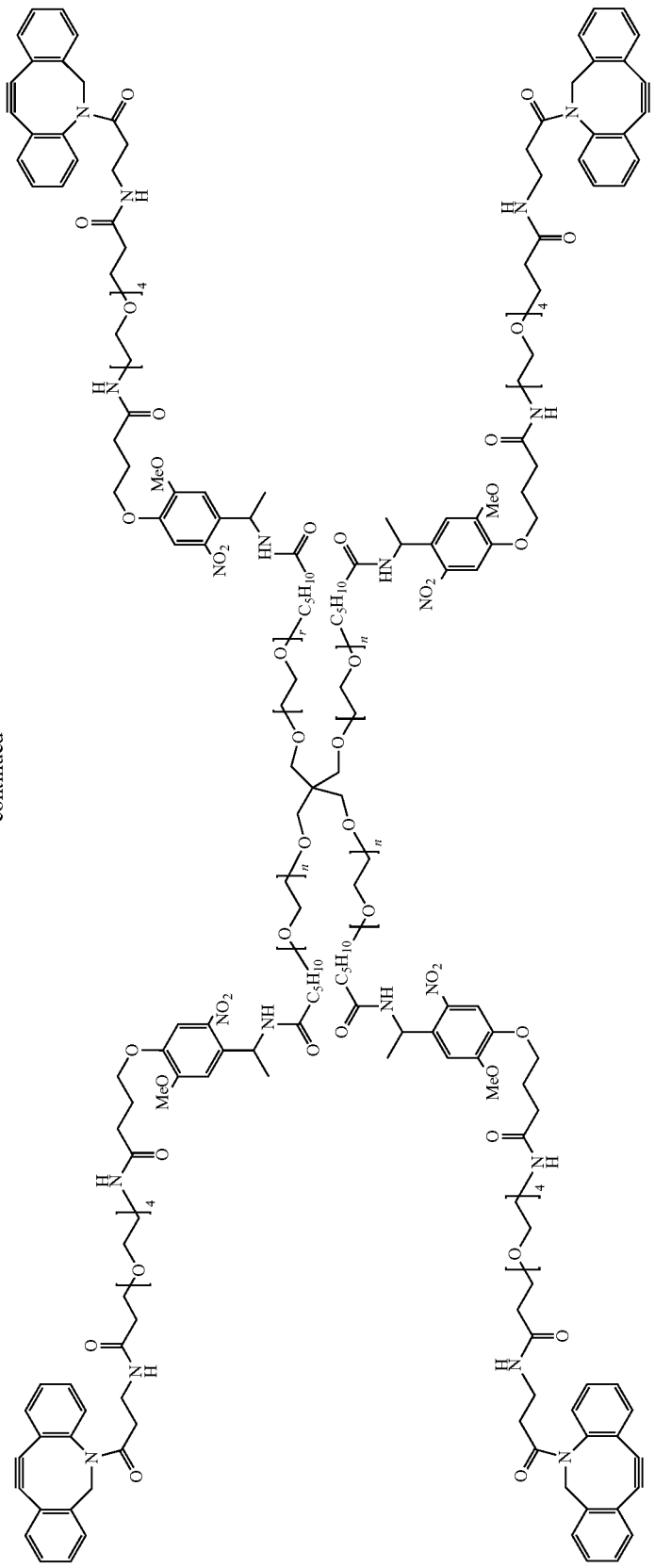

Figure 3A:
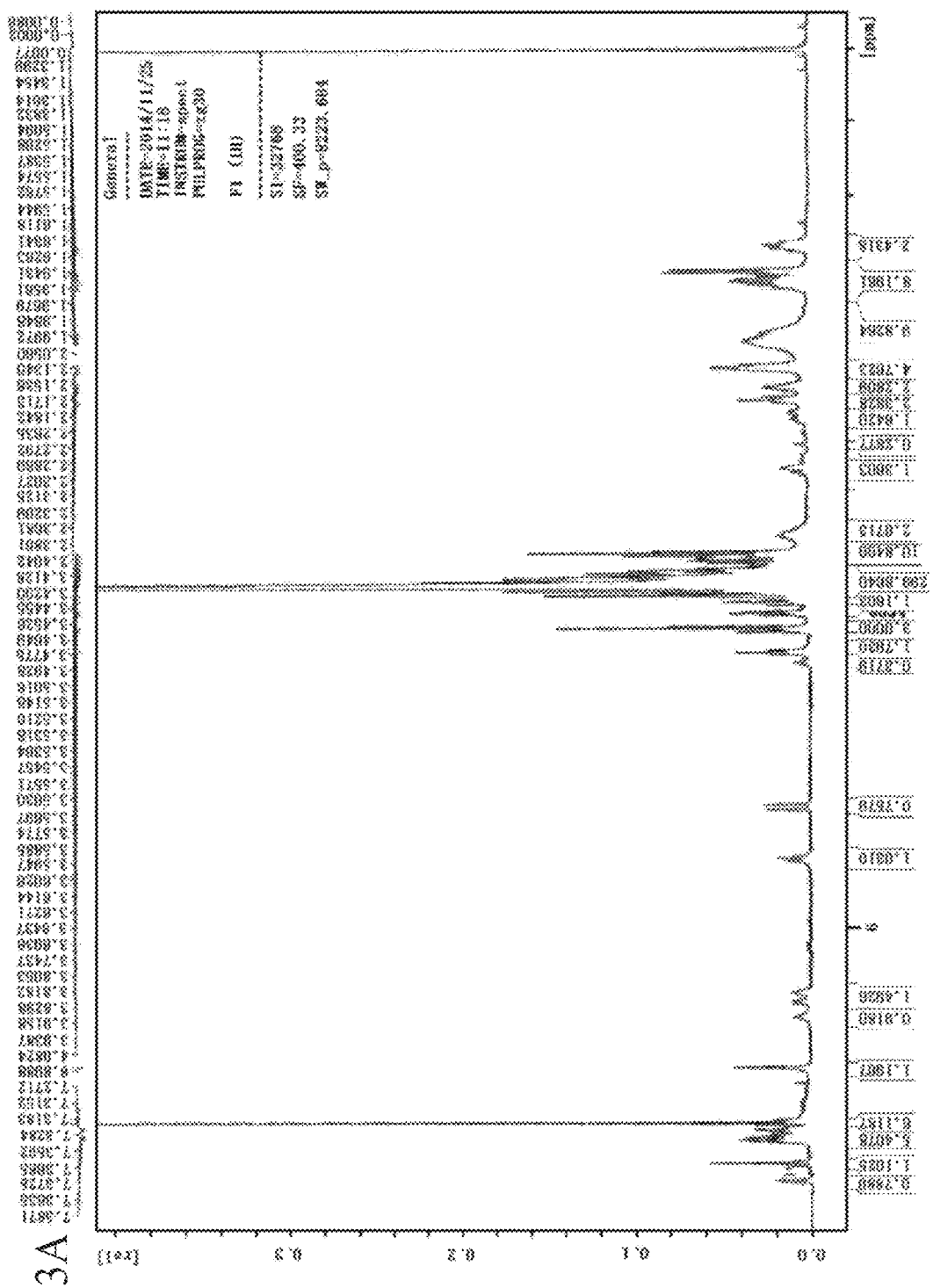
FIG. 3A is a NMR spectrum diagram of synthesized click crosslinking-type photocleavable crosslinker, DBCO-PC-4armPEG. Shown are a ¹H-NMR spectrum of DBCO-PC-4armPEG, and a peak integrated value below.
Figure 3B:
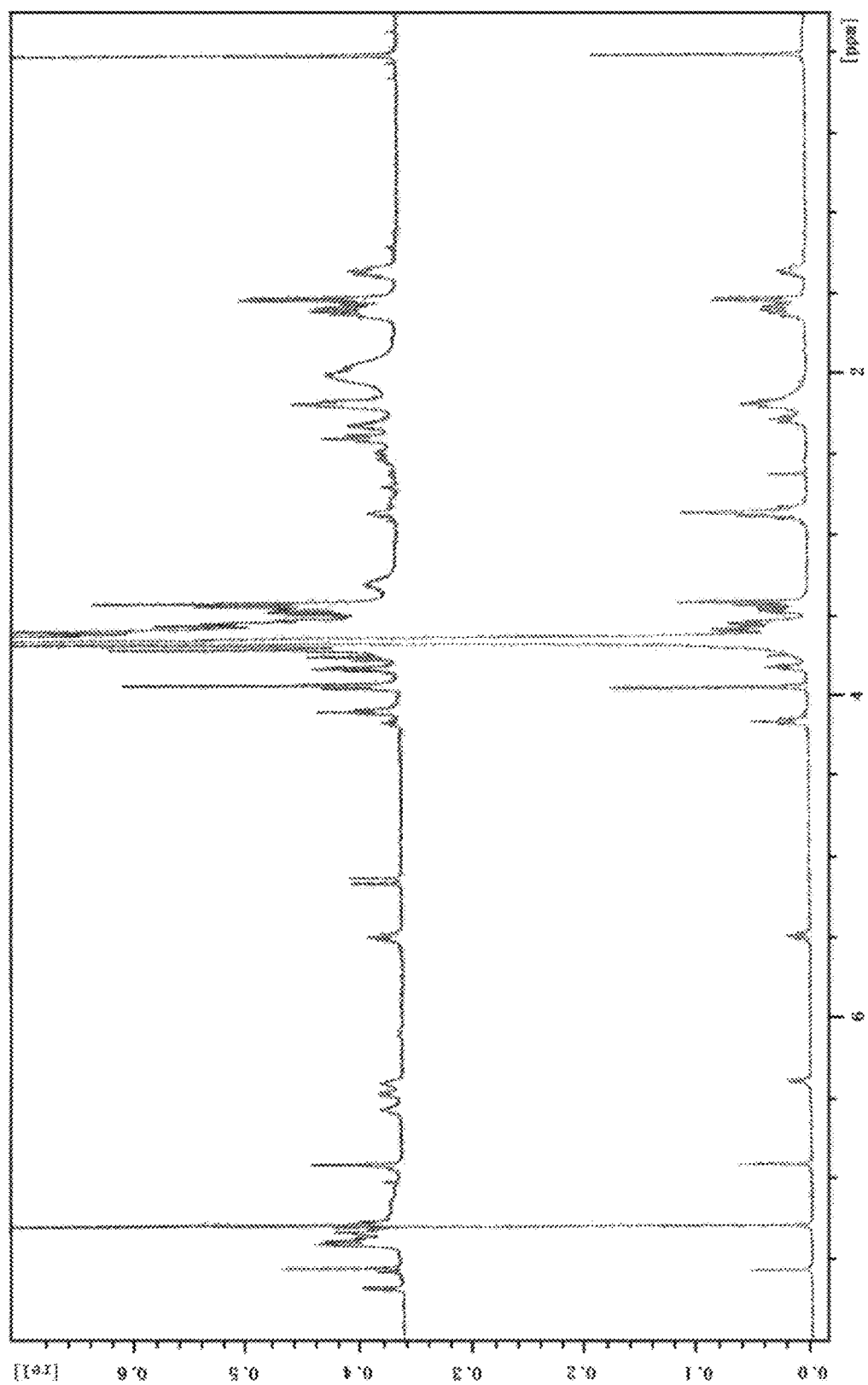
FIG. 3B is a comparative diagram of a ¹H-NMR spectrum of DBCO-PC-4armPEG (above) and NHS-PC-4armPEG (below).
Figure 4A:
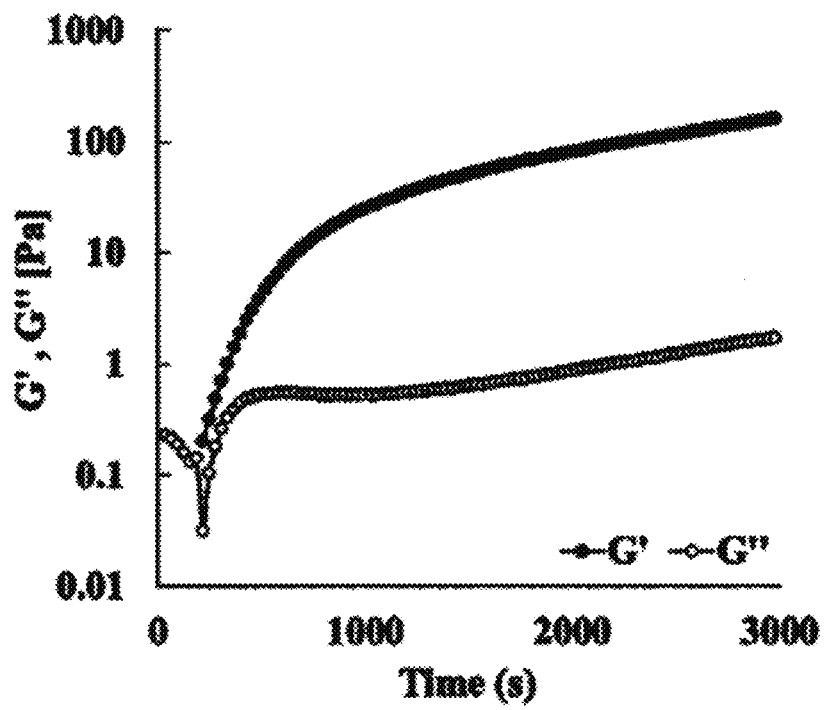
FIG. 4A is a diagram showing changes in a storage modulus (G') and a loss modulus (G") over time when forming a gel by click reaction. A point where G' exceeds G" (crossover point, CP) is a point where gelation occurs. A modulus change when preparing a gel of PD-gelatin (25) is shown. A composition of each gel is shown in Table 7.
Figure 4B:
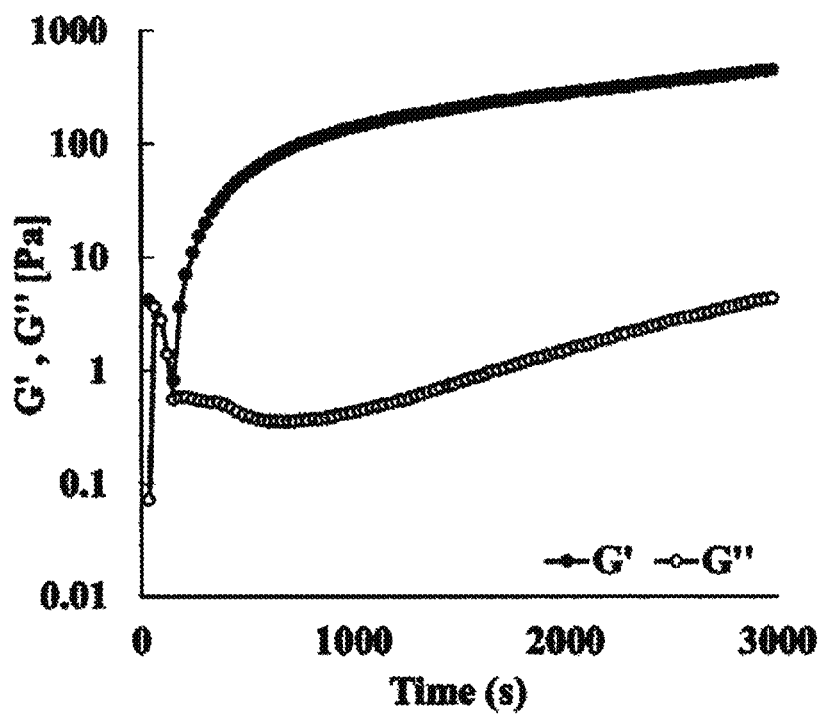
FIG. 4B shows PD-gelatin (50) as same as that of FIG. 4A.
Figure 4C:
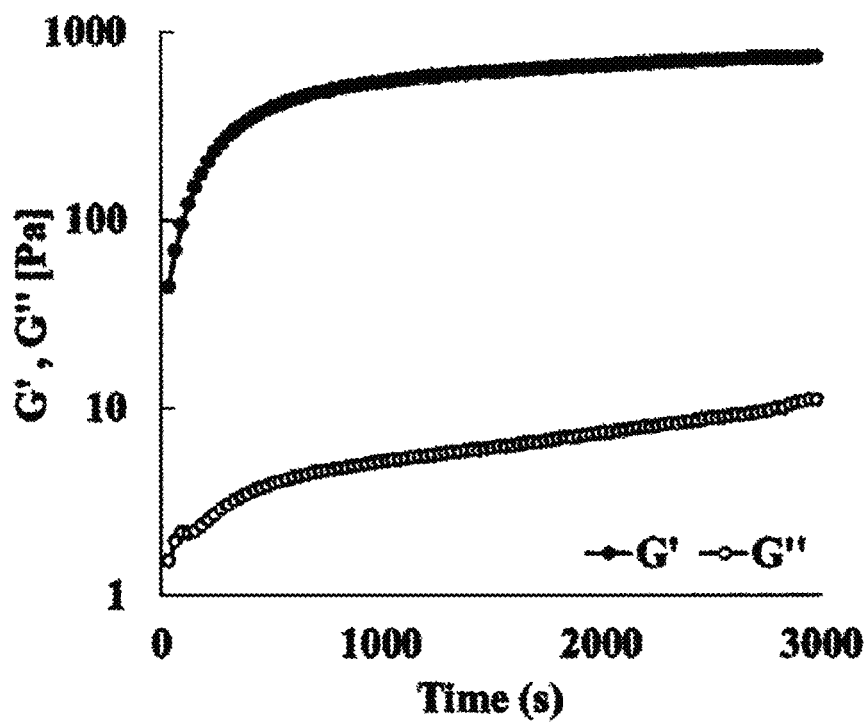
FIG. 4C shows PD-gelatin (75) as same as that of FIG. 4A.
Figure 4D:
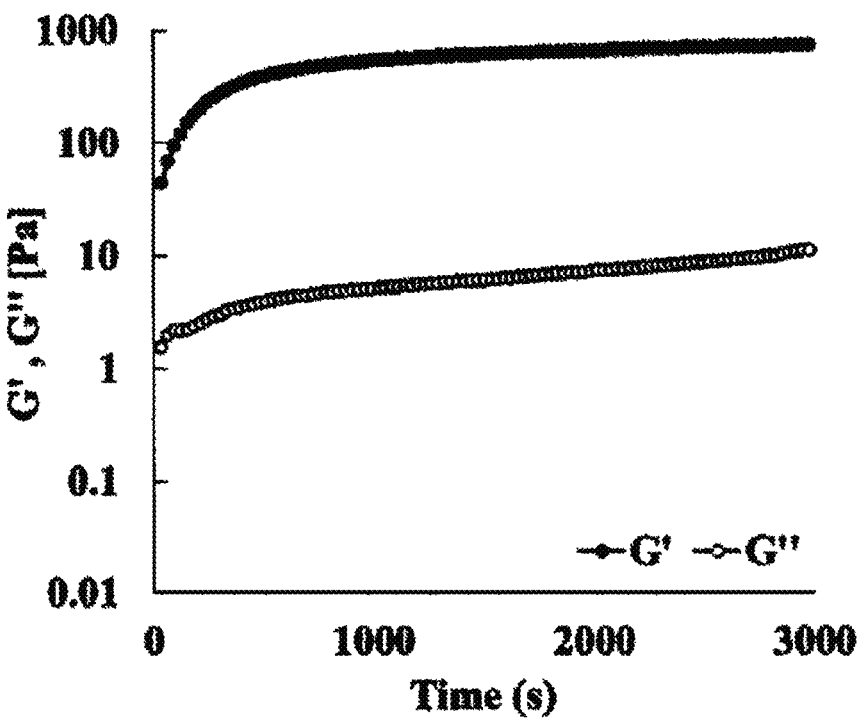
FIG. 4D shows PD-gelatin (100) as same as that of FIG. 4A.

The molecular structure of the synthesized DBCO-PC-4armPEG was checked by $^1$H-NMR in deuterated chloroform (FIG. 3A). It was checked that in DBCO-PC-4armPEG, a peak assigned to DBCO was around 7.3 ppm compared to NHS-PC-4armPEG (FIG. 3B).

Example 4. Evaluation on Photocleavability of DBCO-PC-4ArmPEG

The photocleavage reaction of DBCO-PC-4armPEG was evaluated by changes in the absorption spectrum before and after light irradiation.

In order to measure the absorption spectrum, 120 μM DBCO-PC-4armPEG solution was prepared using 300 mM HEPES of pH 7.4 and 1.5 L thereof was added. The solution in the Eppendorf tube is irradiated with ultraviolet light (365 nm, 25.2 mW/cm$^{-2}$, 0 to 7.6 J) emitted from an ultraviolet light source (UVE-251S, San-Ei Electric, Osaka, Japan) through a 350 nm long wavelength cut filter and a 385 nm short wavelength cut filter. The absorption spectrum was measured at 10° C. using an absorption photometer (Nanodrop, Thermo Fisher Scientific K. K., Kanagawa, Japan).

Figure 1E:
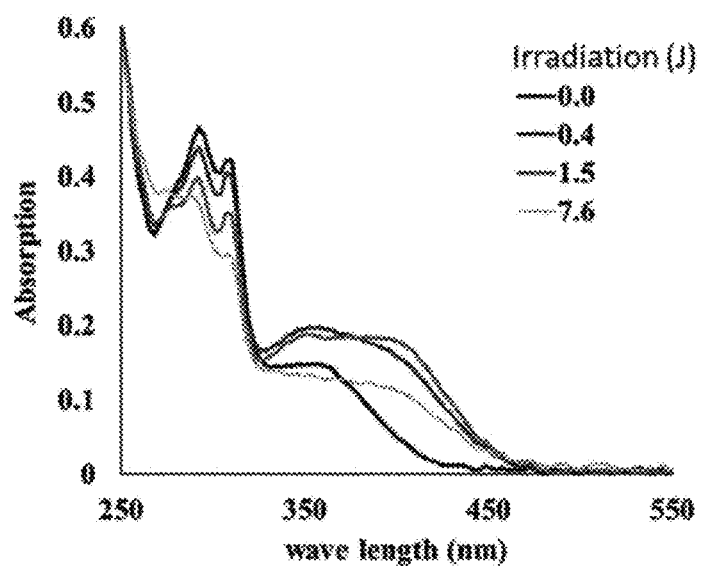
FIG. 1E shows changes in the absorption spectrum of DBCO-PC-4armPEG by light irradiation.

The results are shown in FIG. 1e. An increase in absorption at 390 nm due to the cleavage reaction of an o-nitrobenzyl group was checked by light irradiation at 0.4 J/cm$^{-2}$ or more.

Changes in G' and G" over time when forming a gel by click reaction are shown in FIG. 4. A point where G' exceeds G" (crossover point, CP) is a point where gelation occurs. When four kinds of gels of which a composition is shown in Table 7, which are PD-gelatin (25), PD-gelatin (50), PD-gelatin (75), and PD-gelatin (100), were examined (each shown in FIG. 4A, FIG. 4B, FIG. 4C, and FIG. 4D), in every composition, G' exceeded G" within 5 minutes, and thereafter, an increase in G' was checked over several tens of minutes.

(2) Preparation of Photodegradable Gel Membrane

Azide-modified Gelatin and DBCO-PC-4armPEG were dissolved in 300 mM HEPES buffer of pH 7.4 to be used. Equal amounts of the azide-modified gelatin solution and the DBCO-PC-4armPEG solution were mixed, respectively, so that the final concentrations thereof become concentrations shown in Table 7. The solutions were interposed between Teflon blocks by using a spacer manufactured by Teflon (registered trademark) so that a thickness becomes 300 μm, and incubated at room temperature for 30 minutes to prepare a membrane-like photodegradable gel.

A HEPES buffer containing 1.0 mg/mL Matrigel was used when preparing the azide-modified gelatin solution, followed by mixing with the DBCO-PC-4armPEG solution and molding based on the same protocol as the above protocol, and therefore a membrane-like photodegradable hydrogel containing Matrigel was prepared.

TABLE 7

Mixed concentration of azide-modified gelatin and DBCO-PC-4armPEG (and Matrigel) (after mixing) when preparing photodegradable gel

| Type of hydrogel | Type of azide-gelatin | Azide-gelatin (mg/mL) | DBCO-PC-4amPEG (mM)$^b$ | Matirgel (mg/mL) |
|---|---|---|---|---|
| Gelatin | Gelatin | 12.5 | 0 | 0 |
| PD-gelatin (25) | Azide-gelatin (25) | 12.5 | 0.6 | 0 |
| PD-gelatin (50) | Azide-gelatin (50) | 12.5 | 1.2 | 0 |
| PD-gelatin (75) | Azide-gelatin (75) | 12.5 | 1.8 | 0 |
| PD-gelatin (100) | Azide-gelatin (100) | 12.5 | 2.3 | 0 |
| Gelatin_M+ | Gelatin | 12.5 | 0 | 0.5 |
| PD-gelatin (25)_M+ | Azide-gelatin (25) | 12.5 | 0.6 | 0.5 |
| PD-gelatin (50)_M+ | Azide-gelatin (50) | 12.5 | 1.2 | 0.5 |
| PD-gelatin (75)_M+ | Azide-gelatin (75) | 12.5 | 1.8 | 0.5 |
| PD-gelatin (100)_M+ | Azide-gelatin (100) | 12.5 | 2.3 | 0.5 |

Example 5. Preparation of Photodegradable Gel by Click Reaction Between Azide-Modified Gelatin and DBCO-PC-4ArmPEG (1) Checking of Gel Formation by Rheology Measurement In order to check the sol-gel transition of the click reaction from changes in dynamic viscoelasticity, a storage modulus (G') and a loss modulus (G") was measured by using a rheometer (MCR-302; Anton Paar Ltd., Graz, Austria). Azide-Gelatin and DBCO-PC-4armPEG were dissolved in a HEPES buffer (300 mM, pH 7.4), and then both solutions were mixed in equal amounts, respectively, so that the concentrations thereof become concentrations shown in Table 7 (refer to (2)). Immediately after mixing the two solutions, a device was filled with 500 μL of the mixed solution, and measurement (frequency f: 5 Hz/temperature: 25° C./measurement interval: 30 seconds, 1 hour) was immediately started.

Example 6. Checking of Micropatterned Degradation of Photodegradable Gel by Micropatterned Light Irradiation It was checked that the membrane-like hydrogel prepared in Example 5 was irradiated with micropatterned light and the hydrogel photodegraded according to the micropattern.

Micropatterned light irradiation was carried out using a PC control type microprojection system (DESM-01 Engineering System, Co. Ltd., Nagano, Japan) based on a method of NPL 11.

The pattern to be irradiated was prepared using Adobe illustrator CS4 (Adobe systems software Ireland Ltd.). Micropatterned light having an intensity of 156 mW/cm$^{-2}$ and a wavelength of 365 nm was emitted for 30 seconds and the hydrogel was incubated at 37° C. for 1 hour. Thereafter, the hydrogel was stained with Coomassie Brilliant Blue (CBB, 0.01%) and the micropattern formed in the hydrogel was observed with an inverted microscope (IX-71, Olympus Corporation, Tokyo, Japan).

Figure 5A:
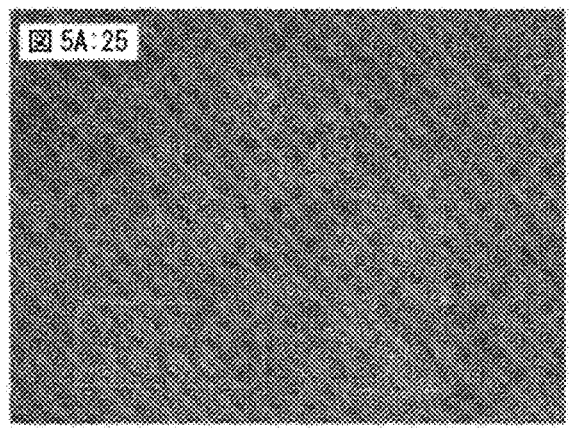
FIG. 5A is a photograph showing the state of micropatterned degradation of a photodegradable gel by micropatterned light irradiation. The state where a gel of PD-gelatin (25) photodegrades is shown. A dark colored portion shows a hydrogel stained with CBB and a light colored portion shows a degrading portion. A composition of each gel is shown in Table 7. A reduction scale is as same as that of FIG. 5D.
Figure 5B:
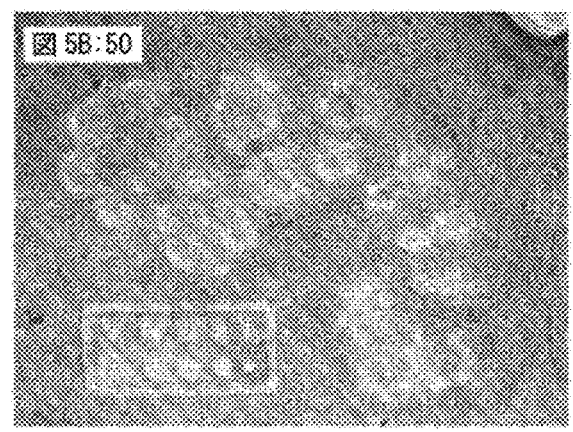
FIG. 5B shows the state where a gel of PD-gelatin (50) photodegrades as same as that of FIG. 5A. A reduction scale is the same as that of FIG. 5D.
Figure 5C:
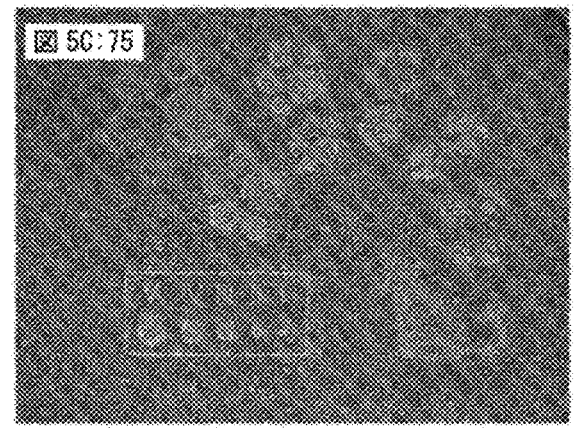
FIG. 5C shows the state where a gel of PD-gelatin (75) photodegrades as same as that of FIG. 5A. A reduction scale is the same as that of FIG. 5D.
Figure 5D:
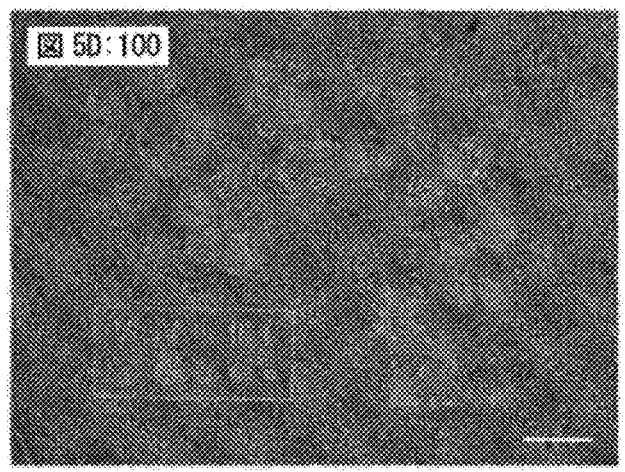
FIG. 5D shows the state where a gel of PD-gelatin (100) photodegrades as same as that of FIG. 5A. A scale bar is 200 µm.
Figure 5E:
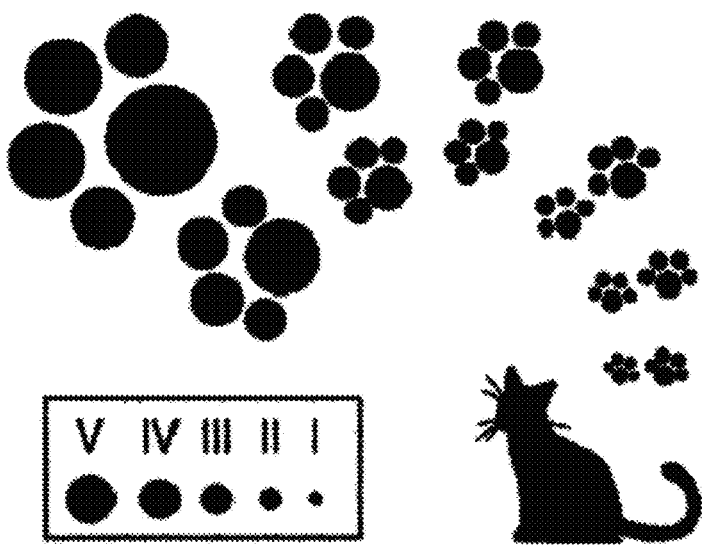
FIG. 5E is an image of an irradiation pattern. A black portion in the irradiation pattern image is an irradiated image.
Figure 6A:
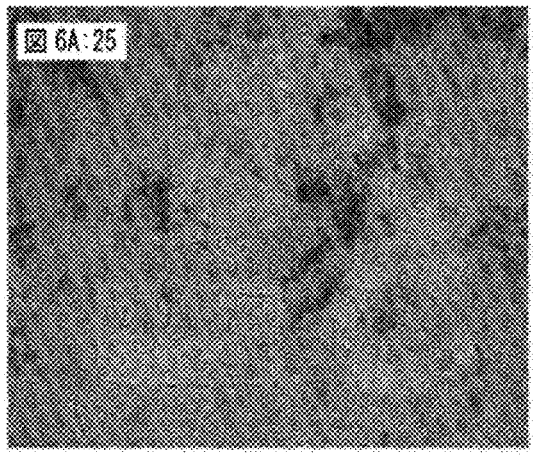
FIG. 6A is a photograph showing the state of micropatterned degradation by micropatterned light irradiation when Matrigel is added to produce the photodegradable gel by using a click-type crosslinker. The state where a gel of PD-gelatin (25)_M+ degrades is shown. A dark colored portion shows a hydrogel stained with CBB and a light colored portion shows a degrading portion. A composition of each gel is shown in Table 7. A reduction scale is the same as that of FIG. 6D.
Figure 6B:
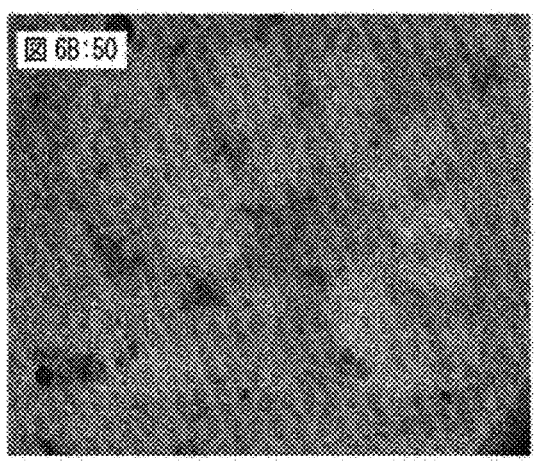
FIG. 6B shows the state where a gel of PD-gelatin (50)_M+ photodegrades as same as that of FIG. 6A. A reduction scale is the same as that of FIG. 6D.
Figure 6C:
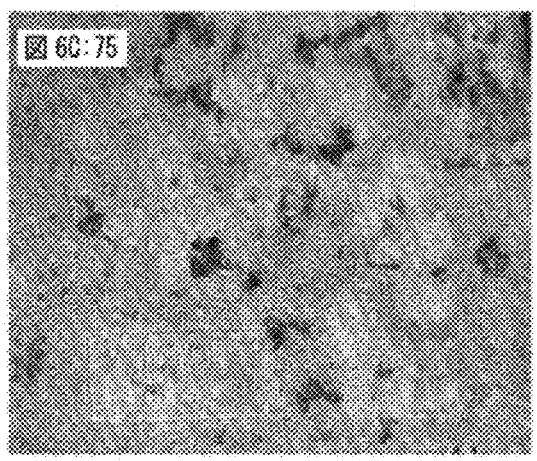
FIG. 6C shows the state where a gel of PD-gelatin (75)_M+ photodegrades as same as that of FIG. 6A. A reduction scale is the same as that of FIG. 6D.
Figure 6D:
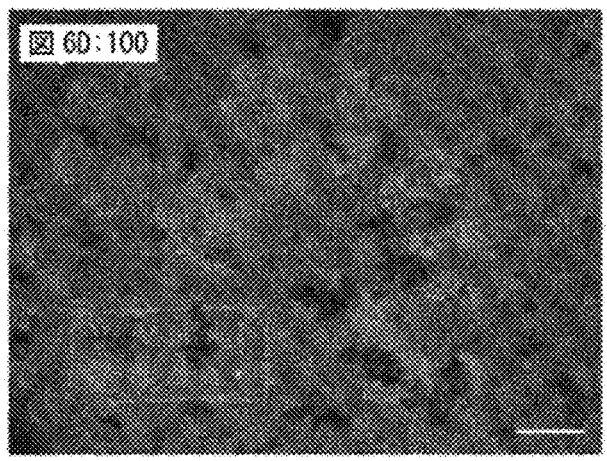
FIG. 6D shows the state where a gel of PD-gelatin (100)_M+ photodegrades as same as that of FIG. 6A. A scale bar is 200 µm.

Regarding the four kinds of gels of which a composition is shown in Table 7, which are PD-gelatin (25), PD-gelatin (50), PD-gelatin (75), and PD-gelatin (100), the results of micropatterned degradation of the photodegradable gel by micropatterned light irradiation are shown in FIGS. 5A to D. After each gel is irradiated with patterned light shown in FIG. 5E, the hydrogel was stained with CBB which is a protein staining reagent. It was checked that the color of the irradiated portion was missing in FIGS. 5A to D, and it was checked that the hydrogel at the irradiated portion degraded according to the irradiation pattern.

Similarly, the four kinds of gels containing Matrigel, of which a composition is shown in Table 7, which are PD-gelatin (25)_M+, PD-gelatin (50)_M+, PD-gelatin (75)_M+, and PD-gelatin (100)_M+, micropatterned degradation of the photodegradable gel by micropatterned light irradiation was performed. The results are shown in FIGS. 6A to D. After each gel is irradiated with patterned light shown in FIG. 5E, the hydrogel was stained with CBB which is a protein staining reagent. It was checked that the color of the irradiated portion was missing in FIG. 6, and it was checked that the hydrogel at the irradiated portion degraded according to the irradiation pattern.

Example 7. Cytotoxicity Test

Cells were embedded in a hydrogel and the survivability of the embedded cells was evaluated with respect to cell damage using Live/Dead cell survival rate assay kit (Life Technologies, Carlsbad, USA) according to the following procedure.

As cells, cells derived from human cervical carcinoma (hereinafter will be referred to as HeLa cells) and cells derived from human prostate cancer (hereinafter will be referred to as DU145 cells) provided by RIKEN BioResource Center were used to be cultured, respectively, at 37° C. under a 5% $CO_2$ environment using Dulbecco's modification of Eagle's medium (DMEM, Life technologies) in which 10% serum was added as a culture medium.

Azide-modified Gelatin and DBCO-PC-4armPEG were dissolved in 300 mM HEPES buffer of pH 7.4 to be used. HeLa cells and DU145 cells were dispersed in an azide-modified gelatin solution at a concentration of $1.4 \times 10^5$ cells/mL. 7 µL of the azide-modified gelatin solution and 7 µL of the DBCO-PC-4armPEG solution were mixed, and were interposed between Teflon blocks by using a spacer manufactured by Teflon so that a thickness becomes 300 µm, and then incubated at room temperature for 30 minutes. After forming the hydrogel, 500 µL of the culture solution was added and cultured at 37° C. for 24 hours under a 5% $CO_2$ environment.

A Live/Dead cell survival rate assay test solution was prepared by adding 1 µL of calcein AM and 4 µL of ethidium homodimer-1 solution to 5 mL of a phosphate buffered saline (PBS). The cells cultured in the hydrogel were washed with PBS, the test solution of the Live/Dead cell survival rate assay was added thereto, followed by incubation at 37° C. for 30 minutes, and then observation was performed using a confocal laser microscope (FV300, Olympus). The living cells and the dead cells were counted so that a total of 100 cells or more was counted for each sample.

Figure 7A:
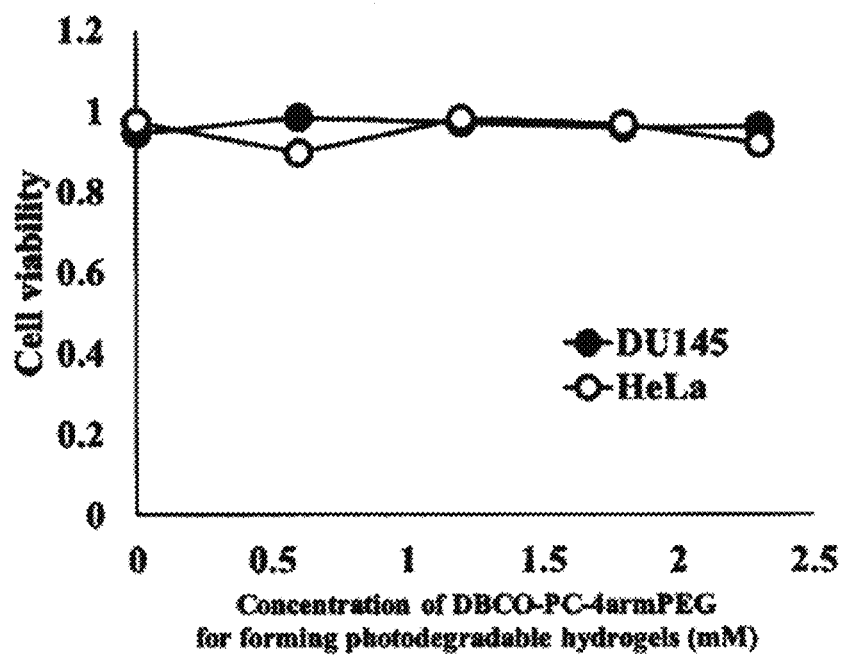
FIG. 7A is a diagram showing a relationship between a concentration of the crosslinker and cell survival rate when DU145 cells and HeLa cells are embedded in the photodegradable gel by using the click-type crosslinker. A composition (Gelatin, PD-gelatin (25), PD-gelatin (50), PD-gelatin (75), PD-gelatin-gelatin (25)_M+, PD-gelatin (50)_M+, PD-gelatin (75)_M+, and PD-gelatin (100)_M+) of each gel in a case where the click-type crosslinker is used is shown in Table 7. Furthermore, in a case where an active ester-type crosslinker is used, a gelatin at a concentration of 25 mg/L is mixed with the active ester-type crosslinker to prepare the photodegradable gel.
Figure 7B:
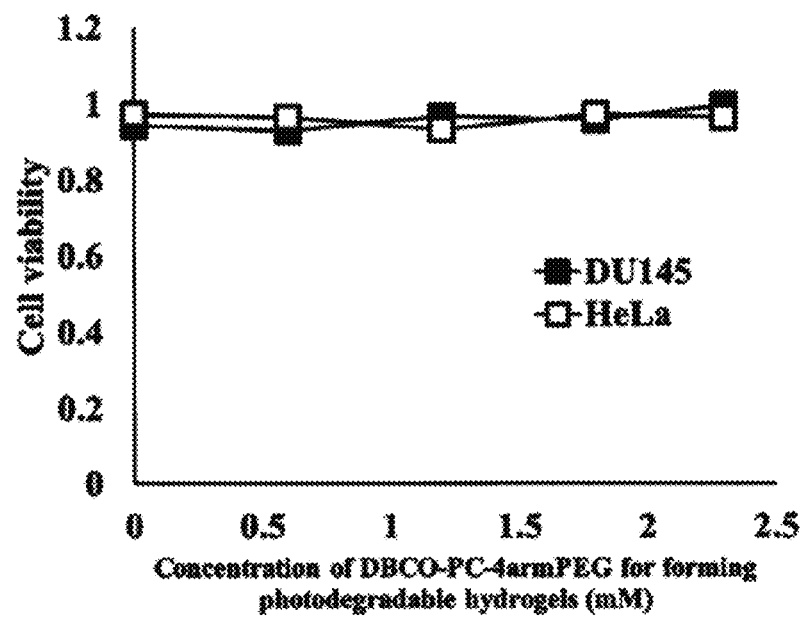
FIG. 7B is a diagram showing a relationship between a concentration of the crosslinker and cell survival rate measured in the same manner as FIG. 7A by using the click-type crosslinker and adding Matrigel.
Figure 7C:
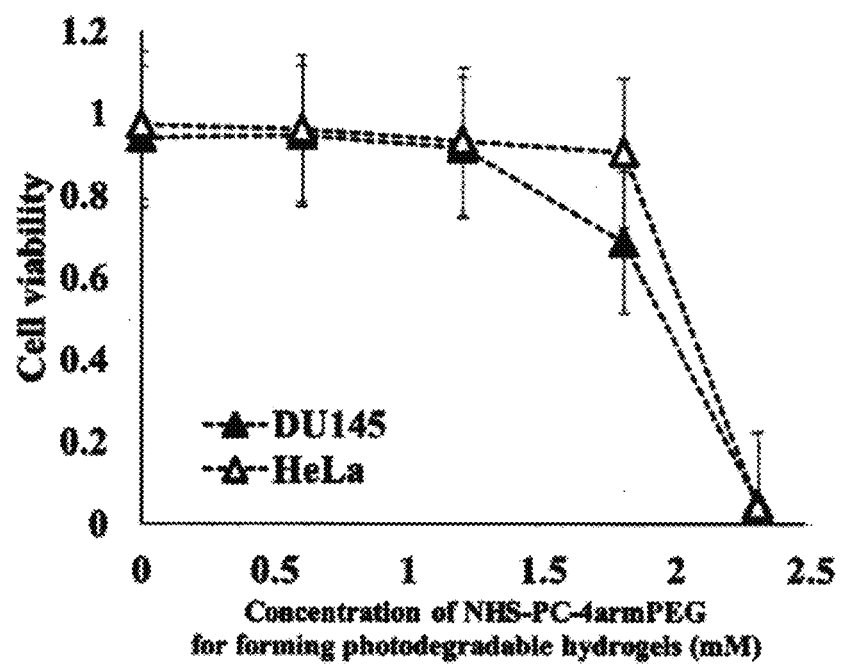
FIG. 7C is a diagram showing a relationship between a concentration of the crosslinker and cell survival rate measured in the same manner as FIG. 7A by using the active ester-type crosslinker.

Regarding the four kinds of hydrogels produced by using azide-modified gelatin and DBCO-PC-4armPEG, of which a composition is shown in Table 7, which are PD-gelatin (25), PD-gelatin (50), PD-gelatin (75), and PD-gelatin (100); the four kinds of hydrogels produced by adding Matrigel, of which a composition is shown in Table 7, which are PD-gelatin (25)_M+, PD-gelatin (50)_M+, PD-gelatin (75)_M+, and PD-gelatin (100)_M+; and the photodegradable hydrogel produced by using gelatin and the active ester-type crosslinker at the same concentration of these hydrogels, the results of investigating the cell survival rate when DU145 cells and HeLa cells were embedded in the photodegradable gel in the manner described above are shown in FIG. 7.

In a case of using the click-type crosslinker and DBCO-PC-4armPEG (FIG. 7A and FIG. 7B), it was checked that the embedded cells showed a high survival rate in a wide concentration range of the crosslinker. On the other hand, in a case of the active ester-type crosslinker (FIG. 7C), it was checked that the survival rate of the cell drastically decreased from the point where the crosslinker concentration exceeds 1.8 mM.

From these results, it was checked that the click-type photocleavable crosslinker of the present embodiment is an excellent crosslinker with lower cytotoxicity compared to the active ester type photocleavable crosslinker shown in the literature of the related art.

Example 8. Cell Culture Test

The culture test of cells embedded in the hydrogel was carried out by the following procedure.

As cells, HeLa cells provided by RIKEN BioResource Center were used to be cultured at 37° C. under a 5% $CO_2$ environment using Dulbecco's modification of Eagle's medium (DMEM, Life technologies) in which 10% serum was added as a culture medium.

A photodegradable hydrogel containing the cells was prepared according to the protocol of Example 7 except that HeLa cells were mixed with an azide gelatin solution at a concentration of $3.3 \times 10^3$ cells/mL. Cell observation was carried out after 24, 48, and 72 hours using an inverted microscope (IX-71, Olympus).

Figure 8A:
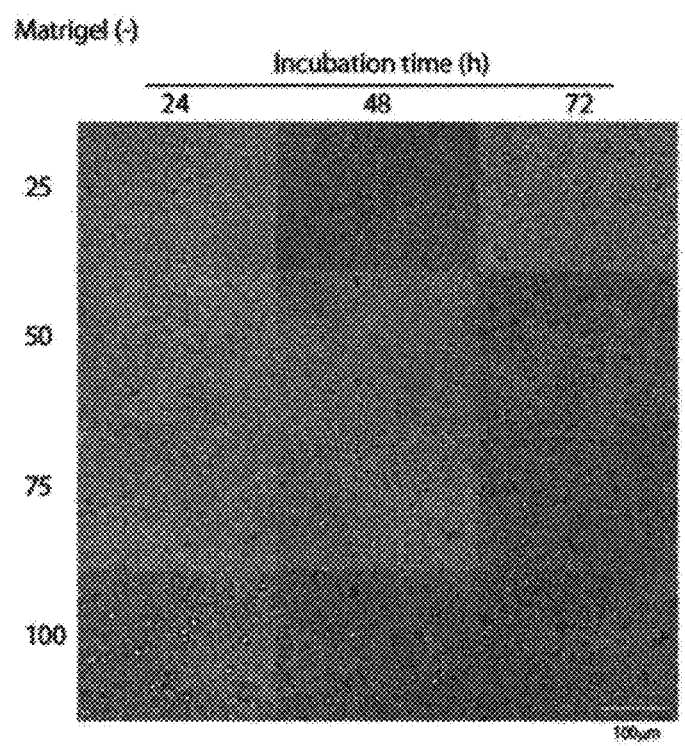
FIG. 8A is a photograph showing the state of growth and form change of HeLa cells embedded in the photodegradable gel. The state in a case where the click-type crosslinker is used is shown. Each of the numbers 25, 50, 75, and 100 on a vertical axis in the drawing shows that the gel embedded in the cells is a gel of PD-gelatin (25), PD-gelatin (50), PD-gelatin (75), and PD-gelatin (100) in Table 7. A scale bar is 100 µm.
Figure 8B:
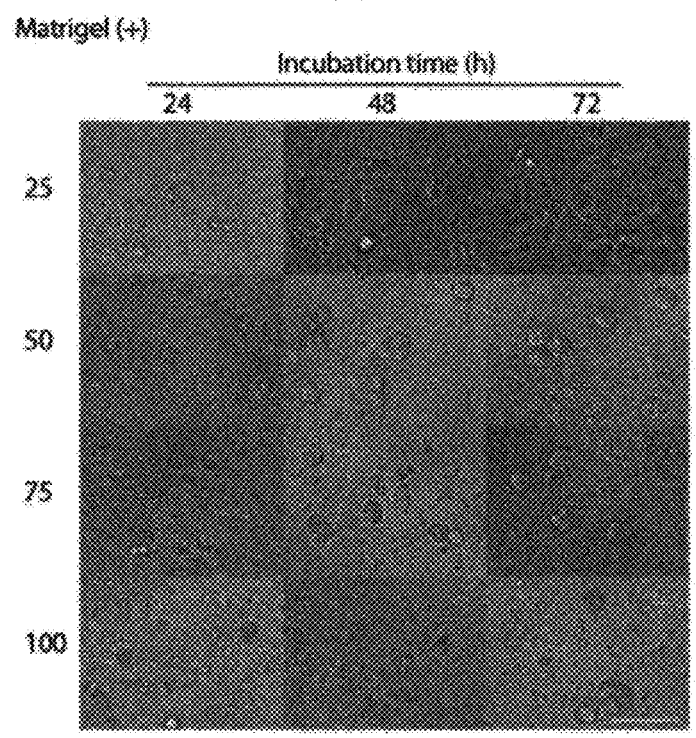
FIG. 8B is a photograph showing the state of growth and form change of HeLa cells embedded in the photodegradable gel. The state in a case where the click-type crosslinker is used and Matrigel is added is shown. Each of the number 25, 50, 75, and 100 on a vertical axis in the drawing indicates PD-gelatin (25)_M+, PD-gelatin (50)_M+, PD-gelatin (75)_M+, and PD-gelatin (100)_M+ in Table 7. A scale bar is 100 µm.

Regarding eight kinds of hydrogels of which a composition is shown in Table 7, which are PD-gelatin (25), PD-gelatin (50), PD-gelatin (75), PD-gelatin (100), PD-gelatin (25)_M+, PD-gelatin (50)_M+, PD-gelatin (75)_M+, and PD-gelatin (100) M+, the state of cell growth and form change when HeLa cells are embedded to be cultured for 3 days according to the procedure described in Example 7 are shown in FIG. 8A and FIG. 8B. It was checked that the cells showed more remarkable growth in the photodegradable hydrogel (FIG. 8B) to which Matrigel was added compared to a system in which Matrigel is not added (FIG. 8A).

From the above results, it was checked that by using the click-type crosslinker, it is possible to form the photodegradable hydrogel even in a system containing an additive factor called Matrigel. It was also checked that the cell growth in the photodegradable hydrogel was remarkable in the presence of Matrigel. It was checked that the click-type photocleavable crosslinker of the present embodiment had better properties than the active ester type photocleavable crosslinker shown in the literature of the related art.

INDUSTRIAL APPLICABILITY

Cell transplantation using cell sheets and cell suspensions is currently the mainstream in regenerative medicine, but in the future, it is considered that regenerative medicine using Engineered Tissue in which tissues having complex structures such as blood vessels and nerves, larger tissues such as liver tissues and kidney tissues, and organs are extracorporeally and artificially processed to be transplanted will become important. In order to extracorporeally and artificially form the large tissue, it is required to form, in the tissue, a network of a blood vessel-like passage for exchanging oxygen, nutrients, and waste products, and a three-dimensional structure thereof inevitably becomes complicated.

A gel that degrades by light can form a complex structure by a combination with micropatterned light irradiation and scan irradiation. The photodegradable gel disclosed in the present invention can be used for processing a tissue having a complex three-dimensional structure, since the gel has low cytotoxicity, the cells can be embedded therein, and the gel degrades by light. The processed tissue can be applied to regenerative medicine.

The photodegradable gel of the present invention can also be used for cell separation. For example, the cells are embedded in the photodegradable gel to be cultured, or in a state where the cells are cultured on the photodegradable gel, the vicinity of the cells to be separated is irradiated with light so that the gel dissolves, and therefore, the cells can be separated. The photodegradable gel of the present invention is a useful material for such cell separation, because the gel has no cytotoxicity, and it is possible to provide the photodegradable gel having cell adhesiveness by a simple method in which two solutions are mixed.

The invention claimed is:

1. A photodegradable hydrogel of which an alkyne group contained in a cyclooctyne ring or an azacyclooctyne ring of the following compound A is modified with the following compound B through an azido group of the compound B:
    (compound A)
    wherein a compound is a photocleavable crosslinker which contains a main chain having a linear type- or a branched type- (of three or more branches) polyethylene glycol structure, a photodegradable nitrobenzyl group disposed at both terminals or a branched terminal of the main chain, and a group having a cyclooctyne ring or an azacyclooctyne ring disposed at a terminal side of the nitrobenzyl group,
    (compound B)
    wherein a compound is an azide-modified protein in which a main chain is a protein and at least some of an amino group present at lysine and arginine side chains of the main chain and an amino group present at a terminal of the main chain are modified with the azido group, and
    wherein the group having a cyclooctyne ring or an azacyclooctyne ring of the compound A is an azadibenzocyclooctyne (DBCO) group.

2. The photodegradable hydrogel according to claim 1, wherein the protein of the compound B includes one or more of cell adhesion proteins selected from gelatin, collagen, laminin, and Matrigel.

3. The photodegradable hydrogel according to claim 1, wherein the average number of repeating ethylene glycol units in the polyethylene glycol structure of the compound A is within a range of 30 to 250.

4. The photodegradable hydrogel according to claim 1, wherein the number of branches in the branched type-main chain of the compound A is 4 or 8.

5. The photodegradable hydrogel according to claim 1, wherein the branched type-main chain of the compound A has a neopentyl skeleton on the center thereof.

6. The photodegradable hydrogel according to claim 1, wherein the photodegradable hydrogel contains a cell growth factor.

7. The photodegradable hydrogel according to claim 1, wherein a modification ratio at which the alkyne group is modified through an azido group is 10% to 100% with respect to the number of the alkyne group.

8. The photodegradable hydrogel according to claim 1, wherein in the compound B, an azido-modification ratio of the amino group in the azide-modified protein is 10% to 100% with respect to the number of the amino group.

9. A culture device,
    wherein the photodegradable hydrogel according to claim 1 is formed on a bottom surface of a culture vessel.

10. A method for forming tissue using the photodegradable hydrogel according to claim 1, the method comprising:
    (I) a step of forming the photodegradable hydrogel in which cells are embedded;
    (II) a step of defining a structure of the photodegradable hydrogel by light irradiation; and
    (III) a step of culturing the cells to form tissue.

11. The method for forming tissue according to claim 10, wherein in the step of defining a structure of the photodegradable hydrogel, light having a light intensity of 0.001 to 1.0 W/cm$^2$ is emitted in the light irradiation, and a structure of the photodegradable hydrogel is defined by CBB staining, fluorescent staining, or microscopic observation.

12. A method for separating cells using the photodegradable hydrogel according to claim 1, the method comprising:
    (I) a step of forming the photodegradable hydrogel in which cells are embedded;
    (II) a step of dissolving the photodegradable hydrogel in a region containing a specific cell among the cells by light irradiation; and
    (III) a step of washing the dissolved photodegradable hydrogel to recover the specific cell in the dissolved region.

13. The method for separating cells according to claim 12, wherein in the step of dissolving the photodegradable hydrogel, light having a wavelength of 300 to 500 nm is emitted in the light irradiation and the photodegradable hydrogel is dissolved by pipetting.

* * * * *